(12) United States Patent
Crosignani et al.

(10) Patent No.: US 9,949,951 B2
(45) Date of Patent: Apr. 24, 2018

(54) PYRROLIDINE-2, 5-DIONE DERIVATIVES, PHARMACEUTICAL COMPOSITIONS AND METHODS FOR USE AS IDO1 INHIBITORS

(71) Applicant: ITEOS THERAPEUTICS, Charleroi (BE)

(72) Inventors: Stefano Crosignani, Nivelles (BE); Sandra Cauwenberghs, Halle (BE); Gregory Driessens, Watermael-Boitsfort (BE); Frederik Deroose, Destelbergen (BE)

(73) Assignee: ITEOS THERAPEUTICS, Charleroi (BE)

( * ) Notice: Subject to any disclaimer, the term of this patent is extended or adjusted under 35 U.S.C. 154(b) by 0 days.

(21) Appl. No.: 15/331,446

(22) Filed: Oct. 21, 2016

(65) Prior Publication Data

US 2017/0035731 A1 Feb. 9, 2017

Related U.S. Application Data

(62) Division of application No. 14/711,911, filed on May 14, 2015, now Pat. No. 9,603,836.

(60) Provisional application No. 61/996,976, filed on May 15, 2014.

(30) Foreign Application Priority Data

May 15, 2014 (EP) .................................. 14168534
Oct. 21, 2014 (BE) .................................. 2014/0754

(51) Int. Cl.
| | | |
|---|---|---|
| A61K 31/404 | (2006.01) | |
| A61K 31/4015 | (2006.01) | |
| C07D 207/408 | (2006.01) | |
| C07D 207/40 | (2006.01) | |
| C07D 403/04 | (2006.01) | |
| C07D 207/46 | (2006.01) | |

(52) U.S. Cl.
CPC ........ A61K 31/404 (2013.01); A61K 31/4015 (2013.01); C07D 207/40 (2013.01); C07D 207/408 (2013.01); C07D 207/46 (2013.01); C07D 403/04 (2013.01)

(58) Field of Classification Search
CPC ........................ A61K 31/404; A61K 31/4015
See application file for complete search history.

(56) References Cited

U.S. PATENT DOCUMENTS

| | | |
|---|---|---|
| 7,151,108 B2 | 12/2006 | Prudhomme et al. |
| 8,008,481 B2 | 8/2011 | Ericsson et al. |
| 9,126,984 B2 | 9/2015 | Crosignani et al. |
| 2003/0109550 A1 | 6/2003 | Clare et al. |
| 2005/0165005 A1 | 7/2005 | Genevois et al. |
| 2009/0118292 A1 | 5/2009 | Deng et al. |
| 2010/0160303 A1 | 6/2010 | Liu et al. |
| 2010/0305133 A1 | 12/2010 | Colon et al. |
| 2010/0317863 A1 | 12/2010 | Kuzmich et al. |
| 2011/0046370 A1 | 2/2011 | Sim et al. |
| 2011/0166143 A1 | 7/2011 | Bretschneider et al. |
| 2012/0053345 A1 | 3/2012 | Ericson et al. |
| 2015/0225367 A1 | 8/2015 | Crosignani et al. |
| 2015/0266857 A1 | 9/2015 | Crosignani et al. |
| 2015/0328228 A1 | 11/2015 | Crosignani et al. |
| 2015/0329525 A1 | 11/2015 | Crosignani et al. |
| 2016/0263087 A1 | 9/2016 | Crosignani et al. |

FOREIGN PATENT DOCUMENTS

| | | |
|---|---|---|
| CN | 101265259 A | 9/2008 |
| EP | 1411057 A1 | 4/2004 |
| JP | 2000-095759 A | 4/2000 |
| WO | WO-1997/043230 A1 | 11/1997 |
| WO | WO-2000/043393 A1 | 7/2000 |
| WO | WO-2003/082869 | 10/2003 |
| WO | WO-2003/101981 A1 | 12/2003 |
| WO | WO2005/058035 A1 | 6/2005 |
| WO | WO-2006/005608 A1 | 1/2006 |
| WO | WO-2006/086484 A1 | 8/2006 |
| WO | WO2007/039580 A1 | 4/2007 |
| WO | WO2007/045622 A1 | 4/2007 |
| WO | WO-2007/050963 A1 | 5/2007 |
| WO | WO-2007/087488 A2 | 8/2007 |
| WO | WO-2007/117465 A2 | 10/2007 |

(Continued)

OTHER PUBLICATIONS

Golub, 1999, Science, vol. 286, No. 531, p. 531-537.*

(Continued)

Primary Examiner — Rebecca L Anderson
Assistant Examiner — Karen Cheng
(74) Attorney, Agent, or Firm — Young & Thompson

(57) ABSTRACT

Uses of compound of Formula I:

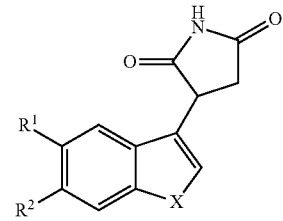

or pharmaceutically acceptable enantiomers, salts, solvates or prodrugs thereof are described. The compounds of Formula I are useful as IDO1 inhibitors. These are also useful for the treatment and/or prevention of cancer and endometriosis.

24 Claims, 7 Drawing Sheets

(56) References Cited

FOREIGN PATENT DOCUMENTS

| | | |
|---|---|---|
| WO | WO-2007/124252 | 11/2007 |
| WO | WO-2008/068621 | 6/2008 |
| WO | WO-2008/073306 A1 | 6/2008 |
| WO | WO-2008/094992 A2 | 8/2008 |
| WO | WO-2008/115804 A1 | 9/2008 |
| WO | WO-2009/015067 A2 | 1/2009 |
| WO | WO-2009/073497 A2 | 6/2009 |
| WO | WO-2009/118292 A1 | 10/2009 |
| WO | WO-2010/008427 A1 | 1/2010 |
| WO | WO-2010/046013 A1 | 4/2010 |
| WO | WO2010/096389 A1 | 8/2010 |
| WO | WO-2010/136491 A1 | 12/2010 |
| WO | WO2011/038163 A1 | 3/2011 |
| WO | WO-2011/046954 A1 | 4/2011 |
| WO | WO-2012/068406 A2 | 5/2012 |
| WO | WO-2012/129338 A1 | 9/2012 |
| WO | WO-2012/161877 A1 | 11/2012 |
| WO | WO-2013/025883 A1 | 2/2013 |
| WO | WO-2015/140717 A1 | 9/2015 |
| WO | WO-2015/173764 | 11/2015 |

OTHER PUBLICATIONS

Targeted Cancer Therapies Fact Sheet, retrieved from http://www.cancer.gov/aboutcancer/treatment/types/targetedtherapies/targetedtherapiesfactsheet on Dec. 8, 2015.*

Dolusic, Tryptophan 2, 3-Dioxygenase (TDO) Inhibitors. 3-(2-(Pyridyl)ethenyl) indoles as Potential Anticancer Immunomodulators, Journal of Medicinal Chemistry, vol. 54(15):5320-5334, Aug. 11, 2011.

Henon, Expedited Synthesis of Substituted Dipyrrolo [3,4-a:3,4-c] carbazole-1,3,4,6-tetraones Structrually Related to Granulatimide, Synthesis, vol. 2006(4):711-715, Jan. 1, 2006.

Henon, Synthesis and biological evaluation of new dipyrrolo [3,4-a:3,4-c] carbazole-1,3,4,6-tetraones, substituted with various saturated and unsaturated side chains via palladium catalyzed cross-coupling reactions, Bioorganic & Medicinal Chemistry, vol. 14(11):3825-3834, Jun. 1, 2006.

Mahboobi, 3-Bromo-4-(1H-3-indolyl)-2, 5-dihydro-1H-2, 5-pyrroledione derivatives as new lead compounds for antibacterially active substances, European Journal of Medicinal Chemistry, vol. 41(2):176-191, Feb. 1, 2006.

Macor, A Direct Synthesis of 3-(Pyrrolidin-3-yl) Indoles for Use as Conformationally Restricted Analogs of Tryptamines, Synthesis, 1997(4):443-449, Apr. 4, 1007.

Muller, Chronic inflammation that facilitates tumor progression creates local immune suppression by inducing indoleamine 2, 3dioxygenase, PNAS, vol. 105(44):17073-17078, Nov. 2008.

Shigemitsu, Synthesis of 3-Methylthio-4-aryl-3-pyrroline-2, 5-diones and 3-Arylpyrrolidine-2, 5-diones by Reaction of Nitroketene Dithioacetal with Arylacetonitriles, Heterocycles, vol. 55(12):2257-2260, Jan. 1, 2001.

Uyttenhove, Evidence for a tumoral immune resistance mechanism based on tryptophan degradation by indoleamine 2, 3-dioxygenase, Nat. Med., vol. 9(10):1269-1274, Oct. 2003.

Chemical Abstracts Service, Database Registry Accession No. 859666-30-1, Aug. 11, 2005.

Cavallo, 2011: The Immune Hallmarks of Cancer, Cancer Immunology Immunotherapy, vol. 60(3):319-326, Nov. 26, 2011.

Hanahan, Hallmarks of Cancer: The Next Generation, Cell, vol. 144:646-674, Mar. 4, 2011.

Hanahan, The Hallmarks of Cancer, Cell, vol. 100:57-70, Jan. 7, 2000.

Kyrgidia, Melanoma: Stem cells, sun exposure and hallmarks for carcinogenesis, molecular concepts and future clinical implications, Journal of Carcinogenesis, vol. 9(1):1-16, Feb. 16, 2010.

Munn et al., Indoleamine 2, 3-dioxygenase and metabolic control of immune responses, Trends Immunol, vol. 34(3):137-143, Mar. 2013.

Munn, Blocking IDO activity to enhance anti-tumor immunity, Front Biosci Elite, vol. 4:734-745, Jan. 2012.

Godin-Ethier et al., Indoleamine 2, 3-dioxygenase expression in human cancers: clinical and immunologic perspectives, Clin Cancer Res, vol. 17:6985-6991, Nov. 2011.

Galon et al. Cancer classification using the immunoscore: a worldwide task force, J Transl Med, vol. 10(205):1-9, Oct. 2012.

Holmgaard et al., Indoleamine 2,3-dioxygenase is a critical resistance mechanism in antitumor T cell immunotherapy targeting CTLA-4, Journal of Experimental Medicine, vol. 210(7):1389-1402. Jul. 2013.

Motz et al., Deciphering and Reversing Tumor Immune Suppression, Immunity, vol. 39(1):61-73. Jul. 25, 2013.

Vippagunta, et al., "Crystalline solids." Advanced drug delivery reviews 48.1 (2001): 3-26.

Golub et al., "Molecular classification of cancer: class discovery and class discovery and class prediction by gene expression monitoring." science 286.5439 (1999): 531-537.

Cancer [Online], [Retrieved on Jul. 6, 2007], Retrieved from the internet, URL http://www.nlm.nih.gov/medlineplus/cancer.html.

Cancer [Online], [Retrieved on Jul. 6, 2007], Retrieved from the internet, URL http://en.wikipedia.org/wiki/Cancer.

Baroni et al., Synthesis of 3-Heteroaryloxindoles through t-BuOCl-Mediated Oxidation of 3-Heteroarylindoles, Synthesis, vol. 2010(23):4075-4081, Oct. 2010.

Beevers, Low molecular weight indole fragments as IMPDH inhibitors, Bioorganic & Medicinal Chemistry Letters, vol. 16(9):2535-2538, May 2006.

Bennett & Plum (EDS), Cecil Textbook of Medicine (20$^{th}$ Ed., vol. 2), W.B. Saunders Company, Philadelphia, pp. 1992-1996 and 2050-2057, Jan. 1996.

Chemical Abstract Service, Database Registry Accession No. 1309341-94-3 (RN, Jun. 14, 2011.

Chemical Abstracts Service, Database Registry Accession No. 1125444-69-0, Mar. 23, 2009.

Chen et al. Synthesis and antiproliferative activity of novel 2-aryl-4-benzoyl-imidazole derivatives targeting tubulin polymerization. Bioorganic & Medicinal Chemistry. vol. 19(16):4782-4795. Aug. 2011.

Comings et al. Exon and intron variants in the human tryptophan 2,3-dioxygenase gene: potential association with Tourette syndrome, substance abuse and other disorders. Pharmacogenetics and Genomics. vol. 6(4):307-318. Aug. 1996.

Davies et al. Tryptophan, Neurodegeneration and HIV-Associated Neurocognitive Disorder. International Journal of Tryptophan Research. vol. 3:121-140. Jun. 2010.

Dolusic et al., "Indoleamine 2,3-dioxygenase inhibitors: a patent review (2008-2012)", Expert Opin. Ther. Pat., vol. 23(10):1367-1381, Aug. 30, 2013.

Fallarino et al., "T cell apoptosis by Tryptophan catabolism", Cell Death Differ., vol. 9(10):1069-1077, Oct. 2002.

FDA mulls drug to slow late-stage Alzheimer's [online], [retrieved on Sep. 23, 2003]. Retrieved form the Internet, URL: Http://www.cnn.com/2003/HEALTH/conditions/09/24/alzheimers.drug.ap/index.html.

Forrest et al. Blood levels of kynurenines, interleukin-23 and soluble human leucocyte antigen-G at different stages of Huntington's disease. Journal of Neurochemistry. vol. 112(1):112-122. Jan. 2010.

Fuvesi et al. The role of kynurenines in the pathomechanism of amyotrophic lateral sclerosis and multiple sclerosis: therapeutic implications. Journal of Neural Transmission. vol. 199(2):225-234. Feb. 2012.

Guo et al. Solubility-Driven Optimization of (Pyridin-3-yl) Benzoxazinyl-oxazolidinones Leading to a Promising Antibacterial Agent. Journal of Medicinal Chemistry. vol. 56(6):2642-2650. Feb. 2013.

Gupton et al., "Preparation of indole containing building blocks for the regiospecific construction of indole appended pyrazoles and pyrroles", Tetrahedron, vol. 69(69):5829-5840, May 2013.

Jakse et al., "Application of alkyl 3-dimethylamino-2-(1H-indol-3-yl)propenoates in the synthesis of 3-heteroarylindoles", Tetrahedron, vol. 60:4601-4608, Mar. 2004.

(56) References Cited

OTHER PUBLICATIONS

Jimenez et al., "4-(1-Phenyl-1H-pyrazol-4-yl)quinolones as novel, selective and brain penetrant metabotropic glutamate receptor 4 positive allosteric modulators", Bioorg. Med. Chem. Let., vol. 22(9):3235-3239, Mar. 7, 2012.
Lahdou et al. Increased serum levels of quinolinic acid indicate enhanced severity of hepatic dysfunction in patients with liver cirrhosis. Human Immunology. vol. 74(1):60-66. Jun. 2012.
Manna et al., UPLC-MS-based urine metabolomics reveals indole-3-lactic acid and phenyllactic acid as conserved biomarkers for alcohol-induced liver disease in the Ppara-null mouse model, J Proteome Res, vol. 10(9):4120-4133, Sep. 2011.
Martin et al. Synthesis of Novel Analogs of Acetyl Coenzyme A: Mimics of Enzyme Reaction Intermediates. Journal of the American Chemical Society. vol. 116(11):4660-4668. Jun. 1994.
Mellor et al., "Creating immune privilege: active local suppression that benefits friends, but protects foes", Nat. Rev. Immunol, vol. 8:74-80, Jan. 2008.
Miller et al. Expression of the kynurenine pathway enzyme tryptophan 2,3-dioxygenase is increased in the frontal cortex of individuals with schizophrenia. Neurobiology of Disease. vol. 15(3):618-629. Apr. 2004.
Munn et al., "Inhibition of T Cell Proliferation by Macrophage Tryptophan Catabolism", J. Exp. Med., vol. 189(9):1363-1372, May 1999.
Munn et al., "Prevention of Allogeneic Fetal Rejection by Tryptophan Catabolism", Science, vol. 281: 1191-1193, Aug. 1998.
Ohta et al. Relationship between the level of serum L-tryptophan and its hepatic uptake and metabolism in rats with carbon tetrachloride-induced liver cirrhosis. Amino Acids. vol. 10(4):369-378. Dec. 1996.
Opitz et al., "An endogenous tumour-promoting ligand of the human aryl hydrocarbon receptor", Nature, vol. 478(7368):197-203, Oct. 2011.
Pilotte et al., "Reversal of tumoral immune resistance by inhibition of tryptophan 2,3-dioxygenase", PNAS, vol. 109(7):2497-2502, Feb. 2012.
Sahm et al. The Endogenous Tryptophan Metabolite and NAD Precursor Quinolinic Acid Confers Resistance of Gliomas to Oxidative Stress. Cancer Research. vol. 73(11):3225-3234. Jun. 2013.
Sperner-Unterweger et al. Enhanced tryptophan degradation in patients with ovarian carcinoma correlates with several serum soluble immune activation markers. Immunobiology. vol. 216(3):269-301. Mar. 2011.
Stone et al. The kynurenine pathway as a therapeutic target in cognitive and neurodegenerative disorders. British Journal of Pharmacology. vol. 169(6):1211-1227. Jul. 2013.
Tilman et al. Human periostin gene expression in normal tissues, tumors and melanoma: evidences for periostin production by both stromal and melanoma cells. Molecular Cancer. vol. 1 6(80):1-13. Dec. 2007.
Turiso et al. Discovery and in Vivo Evaluation of Dual PI3Kβ/δInhibitors. Journal of Medicinal Chemistry. vol. 55(17):7667-7685. Aug. 2012.
Widner et al. Increased neopterin production and tryptophan degradation in advanced Parkinson's disease. Journal of Neural Transmission. vol. 109(2):191-189. Feb. 2002.
Wu et al. Expression of Tryptophan 2,3-Dioxygenase and Production of Kynurenine Pathway Metabolites in Triple Transgenic Mice and Human Alzheimer's Disease Brain. PLOS One. vol. 8(4):e59749. Apr. 2013.
Lala, et al., "Role of nitric oxide in tumor progression: lessons from experimental tumors." Cancer and Metastasis Reviews 17.1 (1998): 91-106.
U.S. Appl. No. 14/076,016, filed Nov. 8, 2013.
U.S. Appl. No. 14/619,589, filed Feb. 11, 2015.
U.S. Appl. No. 61/996,974, filed Feb. 12, 2014.
U.S. Appl. No. 61/996,975, filed Mar. 18, 2014.
U.S. Appl. No. 14/660,082, filed Mar. 17, 2015.
U.S. Appl. No. 61/996,976, filed May 15, 2014.
European Search Report issued on European Application No. 13192224, dated Jan. 14, 2014.
European Search Report issued on European Application No. 14154911, dated Aug. 29, 2014.
European Search Report issued on European Application No. 14160578, dated May 20, 2014.
European Search Report issued on European Application No. 14168534, dated Oct. 21, 2014.
International Search Report and Written Opinion issued on corresponding International Patent Application No. PCT/IB2015/053557.
International Search Report and Written Opinion issued on International Patent Application No. PCT/IB2016/052748.
Notice of Allowance, dated Nov. 14, 2016, issued on U.S. Appl. No. 14/711,911.
Non-Final Office Action, dated Aug. 3, 2016, issued on U.S. Appl. No. 14/711,911 and Response.
Applicant-Initiated Interview summary, dated Oct. 18, 2016, issued on U.S. Appl. No. 14/711,911.
Restriction Requirement, dated Feb. 18, 2016, issued on U.S. Appl. No. 14/711,911 and Response.

* cited by examiner

PYRROLIDINE-2, 5-DIONE DERIVATIVES, PHARMACEUTICAL COMPOSITIONS AND METHODS FOR USE AS IDO1 INHIBITORS

CROSS-REFERENCE TO RELATED APPLICATIONS

This application is a divisional of U.S. patent application Ser. No. 14/711,911, filed May 14, 2015, which claims the benefit of priority of U.S. Provisional Patent Application No. 61/996,976, filed May 15, 2014. These applications are hereby incorporated by reference in their entirety.

FIELD OF INVENTION

The present invention relates to pyrrolidine-2,5-dione derivatives, including pharmaceutically acceptable enantiomers, salts, solvates and prodrugs thereof. Compounds of the invention are inhibitors of IDO1 (indoleamine 2,3-dioxygenase-1) and are useful as therapeutic compounds, particularly in the treatment and/or prevention of cancers.

BACKGROUND OF INVENTION

Indoleamine 2,3-dioxygenase 1 (IDO1) is an intracellular monomeric, heme-containing enzyme that catalyzes the first and rate limiting step of L-tryptophan (Trp) catabolism along the kynurenine pathway, leading to the production of N-formylkynurenine. 95% of Trp is metabolized through this kynurenine pathway. The kynurenine pathway (KYN) initiates the production of neuroactive and immunoregulatory metabolites, collectively known as kynurenines and provides precursors that supplement dietary niacin for the biosynthesis of NAD+ and NADP+.

By locally depleting tryptophan and increasing kynurenines, IDO1 expressed by antigen presenting cells (APCs) such as dendritic cells (plasmacystoid DCs in tumor draining lymph nodes) can greatly affect T-cell proliferation and survival and activate regulatory T cells thereby reducing proinflammatory responses. IDO1 can thus provide "immune privilege" to tissues subject to chronic inflammations such as infectious and allergic diseases, transplantation and cancer. Because such tolerogenic responses can be expected to operate in a variety of physiopathological conditions, tryptophan metabolism and kynurenine production through IDO1 might represent a crucial interface between the immune and nervous system. Expression of IDO1 is upregulated by proinflammatory cytokines and can be detected in a variety of tissues, including placenta, spleen, thymus, lung, digestive tract, and central nervous system (reviewed in Munn et al. Trends Immunol, 2013, 34, 137-43).

IDO1 has emerged as a promising molecular target of new therapeutic agents for treating cancer as well as other diseases characterized by the reduction of local Trp levels and/or to imbalances in the level of cytotoxic metabolites produced by the kynurenine pathway (reviewed in Munn et al. Trends Immunol, 2013, 34, 137-43). Indeed inhibition of IDO1 activity as a therapeutic strategy has been tested in preclinical models of many diseases, with the most widely used IDO1 inhibitor, the tryptophan analogue L-1-methyltryptophan (L-1MT). Treatment with L-1 MT, alone or in combination with other agents, attenuated disease severity in animal models of arthritis, ischemia-reperfusion injury, endotoxin shock, human immunodeficiency virus (HIV)/simian immunodeficiency virus (SIV) infection, airway inflammation, and cancer (Uyttenhove et al., Nat Med, 2003, 9, 10, 1269-1274; Holmgaard et al., J Exp Med, 2013, 210, 7, 1389-1402), among others. For cancer, IDO1 induction has been observed in vivo during rejection of allogeneic tumors, indicating a possible role for this enzyme in the tumor rejection process (Uyttenhove et al., Nat Med, 2003, 9, 10, 1269-1274; Holmgaard et al., J Exp Med, 2013, 210, 7, 1389-1402). Cervical carcinoma cells (or HeLa cells) co-cultured with peripheral blood lymphocytes (PBLs) acquire an immuno-inhibitory phenotype through up-regulation of IDO1 activity. A reduction in PBL proliferation upon treatment with interleukin-2 (IL2) was believed to result from IDO1 released by the tumor cells in response to gamma interferon (IFN)-g ($\gamma$) secretion by the PBLs. IDO1 activity in tumor cells may thus serve to impair anti-tumor responses, a process in which IFNg plays a central role. Further evidence for a tumoral immune resistance mechanism based on tryptophan degradation by IDO1 comes from the observation that most human tumors constitutively express IDO1, and that expression of IDO1 by immunogenic mouse tumor cells prevents their rejection (reviewed in Munn et al., Front Biosci, 2012, 4, 734-45; Godin-Ethier et al. Clin Cancer Res 2011, 17, 6985-6991; Johnson et al. Immunol Invest 2012, 41, 6-7, 765-797). This effect is accompanied by a lack of accumulation of specific T cells at the tumor site and can be partly reverted by systemic treatment of mice with an inhibitor of IDO1, in the absence of noticeable toxicity (Holmgaard et al., J Exp Med, 2013, 210, 7, 1389-1402).

IDO1 expression has been demonstrated by immunohistochemistry in a wide spectrum of cancer patients. IDO1 mRNA, protein or modification of the ratio of tryptophan and kynurenine in the blood have been detected in patients with malignant melanoma, acute myelogenous leukemia, pancreatic, colorectal, prostate, cervical, brain, endometrial and ovarian cancers amongst others. In several malignancies, the presence of IDO1 is an independent predictor of a worse clinical outcome (reviewed in Munn et al., Front Biosci, 2012, 4, 734-45)

Although the potential of the IDO1 inhibitors as pharmaceutical agents has generated a significant interest, the initial inhibitors were identified by modification of Trp but not the discovery of molecules bearing novel structural skeleton. In the early 2000's, the best IDO1 inhibitors were mainly comprised of competitive Trp derivatives (like L-1-MT) and noncompetitive carbolines, which displayed affinities in the micromolar range. Since 2006, some potent nanomolar IDO1 inhibitors with novel structural skeleton have been discovered by high throughput screening, computational screening or natural product isolation and optimization of the core pharmacophores in the structures. Many of these IDO1 inhibitors possess low micromolar activities or limited pharmacokinetics. Two IDO1 inhibitors are currently being tested in phase I/II clinical trials for the treatment of relapsed or refractory solid tumors (reviewed in Dolutit et al., Expert Opin Ther Pat. 2013, 23, 1367-81).

In parallel, the importance of awakening and solidifying tumor immune surveillance is now widely accepted as an important aspect of anti-cancer therapy (Motz et al., Immunity, 2013, 39, 1, 61-73). Immunoscoring of infiltrating T cell subsets is under development as biomarker approach and will allow to determine the patients' responsiveness to treatment (Galon et al., J Transl Med, 2012, 10, 1). Hence, it is still of major interest to find new potent IDO1 inhibitors.

Therefore, there is a need for new IDO1 inhibitors with improved efficacy for cancer treatment and/or prevention.

SUMMARY OF THE INVENTION

The compounds, compositions and methods herein help meet the current need for IDO1 inhibitors which can be administered to any patient diagnosed with cancer, or any subject at risk of developing a cancer.

In one aspect, a pharmaceutical composition or a medicament comprising a compound of Formula Ia is provided:

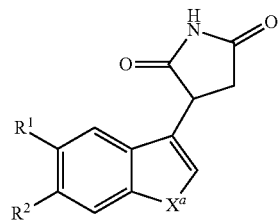

Ia or a pharmaceutically acceptable enantiomer, salt, solvate or prodrug thereof, wherein:

$X^a$ represents —NH— or —$CQ^2$=$CQ^3$-, $Q^2$ and $Q^3$ each independently represent H or C1 to C6 alkyl, preferably $Q^2$ and $Q^3$ each independently represent H or methyl, more preferably $Q^2$ and $Q^3$ represent H;

$R^1$ and $R^2$ each independently represent H, halo, cyano, C1 to C6 alkyl or C1 to C6 alkoxy, preferably $R^1$ and $R^2$ each independently represent H or halo.

In another aspect, a pharmaceutical composition comprising a compound of Formula Ia is provided:

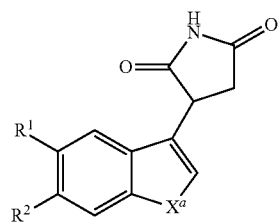

Ia or a pharmaceutically acceptable enantiomer, salt, solvate or prodrug thereof, wherein:

$X^a$ represents —NH— or —$CQ^2$=$CQ^3$-, $Q^2$ and $Q^3$ each independently represent H or C1 to C6 alkyl, preferably $Q^2$ and $Q^3$ each independently represent H or methyl, more preferably $Q^2$ and $Q^3$ represent H, $R^1$ and $R^2$ each independently represent H, halo, cyano, C1 to C6 alkyl or C1 to C6 alkoxy, preferably $R^1$ and $R^2$ each independently represent H or halo;

and at least one pharmaceutically acceptable carrier.

Also provides is a compound of Formula Ia

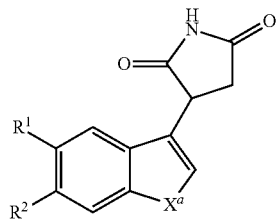

Ia or a pharmaceutically acceptable enantiomer, salt, solvate or prodrug thereof, wherein:

$X^a$ represents —NH— or —$CQ^2$=$CQ^3$-, $Q^2$ and $Q^3$ each independently represent H or C1 to C6 alkyl, preferably $Q^2$ and $Q^3$ each independently represent H or methyl, more preferably $Q^2$ and $Q^3$ represent H, $R^1$ and $R^2$ each independently represent H, halo, cyano, C1 to C6 alkyl or C1 to C6 alkoxy, preferably $R^1$ and $R^2$ each independently represent H or halo.

In one embodiment, the compound of Formula I and/or Formula Ia has a deuterium atom substituted for a hydrogen atom therein, i.e., is optionally deuterated. In one embodiment, the compound of Formula I is deuterated at the chiral carbon and may be used to prepare deuterated compounds of Formula I' and/or Formula I". The compounds described herein, including those of Formula I, Formula Ia, Formula Ib, Formula I' and Formula I", and their deuterated counterparts are useful in the treatment and/or prevention of cancer and endometriosis, and/or for use as IDO1 inhibitor.

Also provided is a compound of Formula Ia'

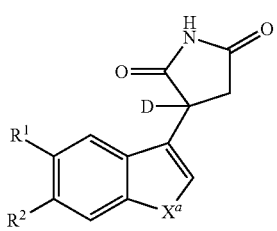

Ia' or a pharmaceutically acceptable enantiomer, salt, solvate or prodrug thereof, wherein:

$X^a$ represents —NH— or —$CQ^2$=$CQ^3$-, $Q^2$ and $Q^3$ each independently represent H or C1 to C6 alkyl, preferably $Q^2$ and $Q^3$ each independently represent H or methyl, more preferably $Q^2$ and $Q^3$ represent H, $R^1$ and $R^2$ each independently represent H, halo, cyano, C1 to C6 alkyl or C1 to C6 alkoxy, preferably $R^1$ and $R^2$ each independently represent H or halo.

In one embodiment, a compound of Formula I and/or Ia is deuterated at the chiral center, as in the structure of Formula Ia'

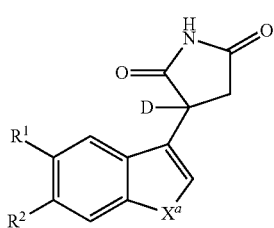

Ia' or a pharmaceutically acceptable enantiomer, salt, solvate or prodrug thereof, wherein:

$X^a$ represents —NH— or —$CQ^2$=$CQ^3$-, $Q^2$ and $Q^3$ each independently represent H or C1 to C6 alkyl, preferably $Q^2$ and $Q^3$ each independently represent H or methyl, more preferably $Q^2$ and $Q^3$ represent H, $R^1$ and $R^2$ each independently represent H, halo, cyano, C1 to C6 alkyl or C1 to C6 alkoxy, preferably $R^1$ and $R^2$ each independently represent H or halo. In one embodiments, racemic compounds of Formula I and/or Ia may be deuterated using the techniques described herein and/or those known to one of skill in the art. Such compounds may be used in a medicament or pharmaceutical composition, and/or production of a deuterated R-enantiomer and/or a deuterated S-enantiomer. Such a deuterated enantiomer may itself be used in a medicament or pharmaceutical composition as described herein.

Further, a compound of Formula I', Formula I", or a mixture thereof is provided:

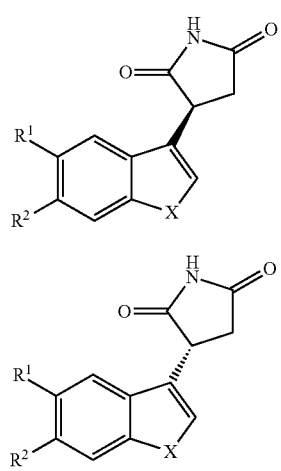

I'

I"

and pharmaceutically acceptable salts, solvates and prodrugs thereof, wherein

X represents —$NQ^1$- or —$CQ^2$=$CQ^3$-, $Q^1$, $Q^2$ and $Q^3$ each independently represent H or C1 to C6 alkyl, preferably $Q^1$ is H, and $Q^2$ and $Q^3$ each independently represent H or methyl, more preferably $Q^1$, $Q^2$ and $Q^3$ each represent H, $R^1$ and $R^2$ each independently represent H, halo, cyano, C1 to C6 alkyl or C1 to C6 alkoxy, preferably $R^1$ and $R^2$ each independently represent H or halo.

In another embodiment, $Q^1$ is H and X represents —NH— or —$CQ^2$=$CQ^3$-, $Q^2$ and $Q^3$ each independently represent H or C1 to C6 alkyl, preferably $Q^2$ and $Q^3$ each independently represent H or methyl, more preferably $Q^2$ and $Q^3$ each represent H, $R^1$ and $R^2$ each independently represent H, halo, cyano, C1 to C6 alkyl or C1 to C6 alkoxy, preferably $R^1$ and $R^2$ each independently represent H or halo.

In another embodiment, a composition comprising a compound of Formula I' and/or Formula I" is provided. The composition may contain a racemic compound. Alternatively, the composition may contain a mixture of a compounds of Formula I' and Formula I", which are produced separately. Such compounds may contain a 1:1 ratio of Formula I' to Formula I", as is present in the racemate, or the R-enantiomer may be present in an amount of greater than 50%. In another alternative, a composition may contain more than 50% of the S-enantiomer. Optionally, the racemate, or one or both of the enantiomers, may be deuterated, e.g., at the chiral carbon.

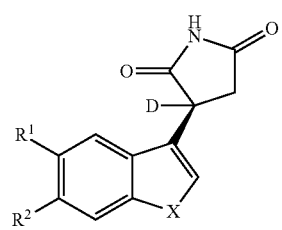

I'a

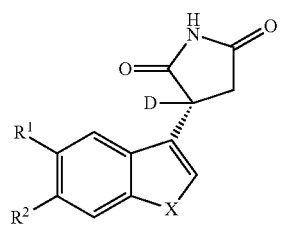

I"a

The invention further discloses a compound of Formula Ib

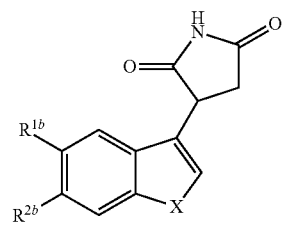

Ib and pharmaceutically acceptable enantiomers, salts, solvates and prodrugs thereof, wherein:

X represents —$NQ^1$- or —$CQ^2$=$CQ^3$-, $Q^1$, $Q^2$ and $Q^3$ each independently represent H or alkyl, preferably $Q^1$ is H, $Q^2$ and $Q^3$ each independently represent H or methyl, more preferably $Q^1$, $Q^2$ and $Q^3$ represent H, $R^{1b}$ and $R^{2b}$ each independently represent H, halo, cyano, alkyl or alkoxy, preferably $R^{1b}$ and $R^{2b}$ each independently represent H or halo;

under the condition that when X represents —$NQ^1$-, then $R^{1b}$ and $R^{2b}$ are not both H, and $R^{1b}$ and $R^{2b}$ are not both F, in one embodiment, Q1 is H.

when X represents —CQ²=CQ³-, then $R^{1b}$ and $R^{2b}$ are not both H.

In another embodiment, when Q1 is H, X represents —NH— or —CQ²=CQ³-

Q² and Q³ each independently represent H or alkyl, Q² and Q³ each independently represent H or methyl, more preferably Q² and Q³ represent H, $R^{1b}$ and $R^{2b}$ each independently represent H, halo, cyano, alkyl or alkoxy, preferably $R^{1b}$ and $R^{2b}$ each independently represent H or halo;

under the condition that when X represents —NH—, then $R^{1b}$ and $R^{2b}$ are not both H, and when X represents —NH—, $R^{1b}$ and $R^{2b}$ are not both F, when X represents —CQ²=CQ³-, then $R^{1b}$ and $R^{2b}$ are not both H.

According to one embodiment, the compound of Formula I' is selected from the group consisting of:
(a) (−)-(R)-3-(5-fluoro-1H-indol-3-yl)pyrrolidine-2,5-dione,
(b) (−)-(R)-3-(1H-indol-3-yl)pyrrolidine-2,5-dione,
(c) (−)-(R)-3-(5-chloro-1H-indol-3-yl)pyrrolidine-2,5-dione,
(d) (R)-3-(6-chloro-5-fluoro-1H-indol-3-yl)pyrrolidine-2,5-dione, or
(e) (R)-3-(6-bromo-5-fluoro-1H-indol-3-yl)pyrrolidine-2,5-dione, or a pharmaceutically acceptable salt or solvate thereof. In another embodiment, the compound of Formula II' is selected from the group consisting of:
(a") (S)-3-(5-fluoro-1H-indol-3-yl)pyrrolidine-2,5-dione,
(b") (S)-3-(1H-indol-3-yl)pyrrolidine-2,5-dione,
(c") (S)-3-(5-chloro-1H-indol-3-yl)pyrrolidine-2,5-dione,
(d") (S)-3-(6-chloro-5-fluoro-1H-indol-3-yl)pyrrolidine-2,5-dione, or
(e") (S)-3-(6-bromo-5-fluoro-1H-indol-3-yl)pyrrolidine-2,5-dione, or a pharmaceutically acceptable salt or solvate thereof. In still another embodiment, the compound of:
3-(6-chloro-5-fluoro-1H-indol-3-yl)pyrrolidine-2,5-dione,
(R)-3-(6-chloro-5-fluoro-1H-indol-3-yl)pyrrolidine-2,5-dione,
3-(6-bromo-5-fluoro-1H-indol-3-yl)pyrrolidine-2,5-dione,
(R)-3-(6-bromo-5-fluoro-1H-indol-3-yl)pyrrolidine-2,5-dione,
3-(naphthalen-1-yl)pyrrolidine-2,5-dione,
3-(6-fluoronaphthalen-1-yl)pyrrolidine-2,5-dione,
3-(7-fluoronaphthalen-1-yl)pyrrolidine-2,5-dione,
3-(6-chloronaphthalen-1-yl)pyrrolidine-2,5-dione, or
3-(7-chloronaphthalen-1-yl)pyrrolidine-2,5-dione
or a pharmaceutically acceptable salt or solvate thereof, or a deuterated form thereof.

The invention also discloses a process for manufacturing a compound of Formula I', I" or Ib, comprising: reacting maleimide with a compound of Formula (i) or (ib)

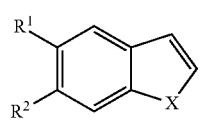

(i)

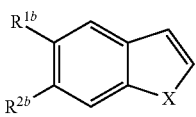

(ib)

wherein X, $R^1$ and $R^2$ are as defined in Formula I' or I" and $R^{1b}$ and $R^{2b}$ are as defined in Formula Ib, and optionally separating enantiomers.

In another aspect, a compound having the structure of Formula II':

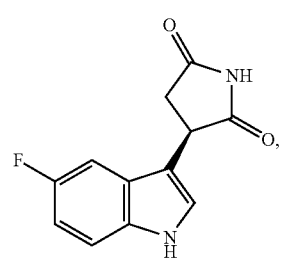

II' or a pharmaceutically acceptable salt or solvate thereof is provided. In one embodiment, the compound is a free base, i.e., is in neither salt nor solvate form. Also provided a pharmaceutical compositions containing a compound of Formula II' alone, or optionally mixed or blended with a compound having the structure of Formula II":

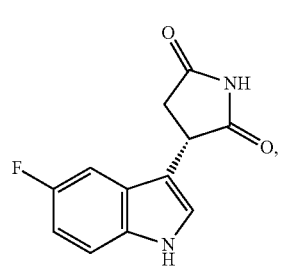

II"

or a pharmaceutically acceptable salt thereof.

Other aspects and advantages of the invention will be apparent from the following detailed description of the invention.

BRIEF DESCRIPTION OF THE DRAWINGS

FIG. 3 shows the tumor growth of 4T1 tumors after treatment with compound 1 at a dose of 100 mg/kg BID. The upper line represents vehicle and the lower line represents compound 1.

DETAILED DESCRIPTION OF THE INVENTION

Compounds

Compounds of Formula I

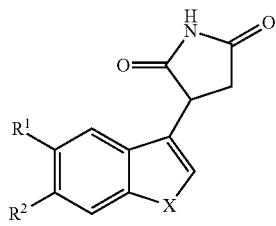

Figure 1:
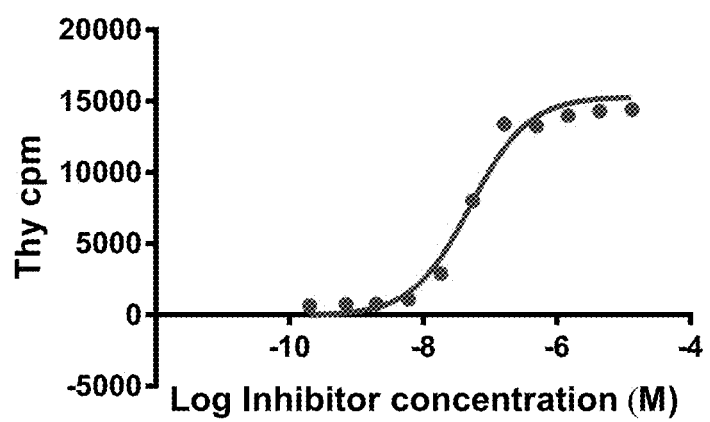
FIG. 1 is a graph showing the effect of increasing amounts of compound 2 of the invention on T-cell proliferation (as measured by Thymidine incorporation) in a SKOV-3 PBMC co-culture assay.

I and pharmaceutically acceptable enantiomers, salts, solvates and prodrugs thereof, wherein:

X represents —NQ$^1$— or —CQ$^2$=CQ$^3$—,

Q$^1$, Q$^2$ and Q$^3$ each independently represent H or alkyl, preferably Q$^1$, Q$^2$ and Q$^3$ each independently represent H or methyl, more preferably Q$^1$, Q$^2$ and Q$^3$ represent H, R$^1$ and R$^2$ each independently represent H, halo, cyano, alkyl or alkoxy, preferably R$^1$ and R$^2$ each independently represent H or halo.

In another embodiment, Q$^1$ is H, X represents —NH— or —CQ$^2$=CQ$^3$—;

Q$^2$ and Q$^3$ each independently represent H or alkyl, preferably Q$^2$ and Q$^3$ each independently represent H or methyl, more preferably Q$^2$ and Q$^3$ represent H, R$^1$ and R$^2$ each independently represent H, halo, cyano, alkyl or alkoxy, preferably R$^1$ and R$^2$ each independently represent H or halo.

Also provided herein are compound of Formula I, and pharmaceutically acceptable enantiomers, salts, solvates and prodrugs thereof, which have at least one deuterium atom substituted for a hydrogen atom. In one embodiment, a compound of Formula I, or any of its subformulae provided herein, including Ia, Ib, I', I, II, II', II'', at the chiral center, as illustrated below in the structure of Formula Ia'

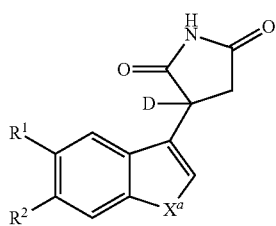

Ia' or a pharmaceutically acceptable enantiomer, salt, solvate or prodrug thereof. Formulae I, Ia and Ib are drawn without reference to stereochemistry, and thus each encompasses a racemic compound, and separate stereoisomers, i.e., the R- and/or S-stereoisomer. In one embodiment, these stereoisomers may have the structure of Formula I' (R-stereoisomer) and Formula II' (S-enantiomer).

Illustrative compounds of Formula I are shown in the table and examples herein and include:
3-(5-fluoro-1H-indol-3-yl)pyrrolidine-2,5-dione,
(−)-(R)-3-(5-fluoro-1H-indol-3-yl)pyrrolidine-2,5-dione,
(+)-(S)-3-(5-fluoro-1H-indol-3-yl)pyrrolidine-2,5-dione,
3-(1H-indol-3-yl)pyrrolidine-2,5-dione,
(−)-(R)-3-(1H-indol-3-yl)pyrrolidine-2,5-dione,
(+−)-(S)-3-(1H-indol-3-yl)pyrrolidine-2,5-dione,
3-(5-chloro-1H-indol-3-yl)pyrrolidine-2,5-dione,
(−)-(R)-3-(5-chloro-1H-indol-3-yl)pyrrolidine-2,5-dione,
(+)-(S)-3-(5-chloro-1H-indol-3-yl)pyrrolidine-2,5-dione,
3-(6-chloro-5-fluoro-1H-indol-3-yl)pyrrolidine-2,5-dione,
(R)-3-(6-chloro-5-fluoro-1H-indol-3-yl)pyrrolidine-2,5-dione,
(S)-3-(6-chloro-5-fluoro-1H-indol-3-yl)pyrrolidine-2,5-dione,
3-(6-bromo-5-fluoro-1H-indol-3-yl)pyrrolidine-2,5-dione,
(R)-3-(6-bromo-5-fluoro-1H-indol-3-yl)pyrrolidine-2,5-dione,
(S)-3-(6-bromo-5-fluoro-1H-indol-3-yl)pyrrolidine-2,5-dione,
3-(5-bromo-1H-indol-3-yl)pyrrolidine-2,5-dione,
3-(5-methyl-1H-indol-3-yl)pyrrolidine-2,5-dione,
3-(5-methoxy-1H-indol-3-yl)pyrrolidine-2,5-dione,
3-(2,5-dioxopyrrolidin-3-yl)-1H-indole-5-carbonitrile,
3-(5,6-difluoro-1H-indol-3-yl)pyrrolidine-2,5-dione,
3-(5-fluoro-6-methyl-1H-indol-3-yl)pyrrolidine-2,5-dione,
3-(6-fluoro-1H-indol-3-yl)pyrrolidine-2,5-dione,
3-(6-chloro-1H-indol-3-yl)pyrrolidine-2,5-dione,
3-(6-bromo-1H-indol-3-yl)pyrrolidine-2,5-dione,
3-(6-methyl-1H-indol-3-yl)pyrrolidine-2,5-dione,
3-(6-methoxy-1H-indol-3-yl)pyrrolidine-2,5-dione,
3-(2,5-dioxopyrrolidin-3-yl)-1H-indole-6-carbonitrile,
3-(naphthalen-1-yl)pyrrolidine-2,5-dione,
3-(6-fluoronaphthalen-1-yl)pyrrolidine-2,5-dione,
3-(7-fluoronaphthalen-1-yl)pyrrolidine-2,5-dione,
3-(6-chloronaphthalen-1-yl)pyrrolidine-2,5-dione, and
3-(7-chloronaphthalen-1-yl)pyrrolidine-2,5-dione.

Optionally, these compounds of Formula I may be deuterated, e.g., at the chiral center. An illustrated deuterated compound (3-$^2$H)-3-(5-fluoro-1H-indol-3-yl)pyrrolidine-2,5-dione is provided in the examples below. Other deuterated compounds may include, e.g.,
(−)-(R)-(3-$^2$H)-3-(5-fluoro-1H-indol-3-yl)pyrrolidine-2,5-dione,
(+)-(S)-(3-$^2$H)-3-(5-fluoro-1H-indol-3-yl)pyrrolidine-2,5-dione,
(3-$^2$H)-3-(1H-indol-3-yl)pyrrolidine-2,5-dione,
(−)-(R)-(3-$^2$H)-3-(1H-indol-3-yl)pyrrolidine-2,5-dione,
(+−)-(S)-(3-$^2$H)-3-(1H-indol-3-yl)pyrrolidine-2,5-dione,
(3-$^2$H)-3-(5-chloro-1H-indol-3-yl)pyrrolidine-2,5-dione,
(−)-(R)-(3-$^2$H)-3-(5-chloro-1H-indol-3-yl)pyrrolidine-2,5-dione,
(+)-(S)-(3-$^2$H)-3-(5-chloro-1H-indol-3-yl)pyrrolidine-2,5-dione,
(3-$^2$H)-3-(6-chloro-5-fluoro-1H-indol-3-yl)pyrrolidine-2,5-dione,
(R)-(3-$^2$H)-3-(6-chloro-5-fluoro-1H-indol-3-yl)pyrrolidine-2,5-dione,
(S)-(3-$^2$H)-3-(6-chloro-5-fluoro-1H-indol-3-yl)pyrrolidine-2,5-dione, (3-²H)-3-(6-bromo-5-fluoro-1H-indol-3-yl)pyrrolidine-2,5-dione,
(R)-3-(6-bromo-5-fluoro-1H-indol-3-yl)pyrrolidine-2,5-dione,
(S)-(3-²H)-3-(6-bromo-5-fluoro-1H-indol-3-yl)pyrrolidine-2,5-dione,
(3-²H)-3-(5-bromo-1H-indol-3-yl)pyrrolidine-2,5-dione,
(3-²H)-3-(5-methyl-1H-indol-3-yl)pyrrolidine-2,5-dione,
(3-²H)-3-(5-methoxy-1H-indol-3-yl)pyrrolidine-2,5-dione,
3-(2,5-dioxopyrrolidin-3-yl)-1H-indole-5-carbonitrile,
(3-²H)-3-(5,6-difluoro-1H-indol-3-yl)pyrrolidine-2,5-dione,
(3-²H)-3-(5-fluoro-6-methyl-1H-indol-3-yl)pyrrolidine-2,5-dione,
(3-²H)-3-(6-fluoro-1H-indol-3-yl)pyrrolidine-2,5-dione,
(3-²H)-3-(6-chloro-1H-indol-3-yl)pyrrolidine-2,5-dione,
(3-2H)-3-(6-bromo-1H-indol-3-yl)pyrrolidine-2,5-dione,
(3-²H)-3-(6-methyl-1H-indol-3-yl)pyrrolidine-2,5-dione,
(3-²H)-3-(6-methoxy-1H-indol-3-yl)pyrrolidine-2,5-dione,
(3-²H)-3-(2,5-dioxopyrrolidin-3-yl)-1H-indole-6-carbonitrile,
(3-²H)-3-(naphthalen-1-yl)pyrrolidine-2,5-dione,
(3-²H)-3-(6-fluoronaphthalen-1-yl)pyrrolidine-2,5-dione,
(3-²H)-3-(7-fluoronaphthalen-1-yl)pyrrolidine-2,5-dione,
(3-²H)-3-(6-chloronaphthalen-1-yl)pyrrolidine-2,5-dione, and
(3-²H)-3-(7-chloronaphthalen-1-yl)pyrrolidine-2,5-dione, In one embodiment, preferred compounds of Formula I are those of Formula I' or I"

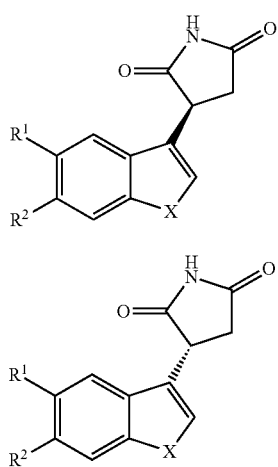

and pharmaceutically acceptable, salts, solvates and prodrugs thereof, wherein X, $R^1$ and $R^2$ are as defined in Formula I.

As described herein, a racemic compound of Formula I may contain about 50% of a compound of Formula I' and about 50% of Formula I" based on a molar ratio (about 48 to about 52 mol %, or about a 1:1 ratio)) of one of the isomers. In another embodiment, a composition, medicament, or method of treatment may involve combining separately produced compounds of Formula I' and Formula I" in an approximately equal molar ratio (about 48 to 52%). In another embodiment, a medicament or pharmaceutical composition may contain a mixture of separate compounds of Formula I' and Formula I" in different ratios. In one embodiment, the pharmaceutical composition contains an excess (greater than 50%) of the R-enantiomer (Formula I'). Suitable molar ratios of R/S may be from about 1.5:1, 2:1, 3:1, 4:1, 5:1, 10:1, or higher. In another embodiment, a pharmaceutical composition may contain an excess of the S-enantiomer (Formula I"), with the ratios provided for R/S reversed. Other suitable amounts of R/S may be selected. For example, the R-enantiomer may be present in amounts of at least about 55% to 100%, or at least 65%, at least 75%, at least 80%, at least 85%, at least 90%, about 95%, about 98%, or 100%. In other embodiments, the S-enantiomer may be present in a higher percentage, e.g., in amounts of at least about 55% to 100%, or at least 65%, at least 75%, at least 80%, at least 85%, at least 90%, about 95%, about 98%, or 100%. Ratios between all these exemplary embodiments as well as greater than and less than them while still within the invention, all are included. (The term "ratio" as used herein (above and below) refers always to the molar ratio). Compositions may contain a mixture of the racemate and a separate compound of Formula I' and/or Formula I", in free base and/or in salt form.

Optionally, the racemate, or one or both of the enantiomers, may be deuterated. Such deuterated compounds may be in salt form. For example, the deuterated stereoisomers may be characterized by the structure:

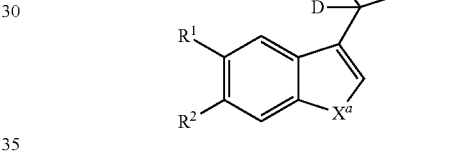

wherein X (or $X^a$), $R^1$, and $R^2$ are as defined above in Formula I and Ia. Without wishing to be bound by theory, it has been described in the literature generally that one enantiomer (isomer or stereoisomer) can convert in plasma to the racemate and/or to the other enantiomer. It is believed that deuteration at the chiral center of these compounds slows the conversion of the individual stereoisomers to the racemate and/or the other stereoisomer in plasma.

In one embodiment, preferred compounds of Formula I are those of Formula Ia

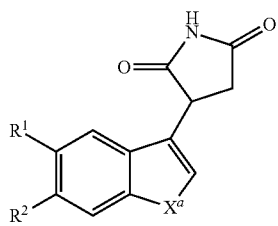

and pharmaceutically acceptable enantiomers, salts, solvates and prodrugs thereof, wherein:
$X^a$ represents —NH— or —$CQ^2$=$CQ^3$-,
$Q^2$ and $Q^3$ each independently represent H or alkyl, preferably $Q^2$ and $Q^3$ each independently represent H or methyl, more preferably $Q^2$ and $Q^3$ represent H,
$R^1$ and $R^2$ each independently represent H, halo, cyano, alkyl or alkoxy, preferably $R^1$ and $R^2$ each independently represent H or halo.

In one embodiment, preferred compounds of Formula I are those of Formula Ib

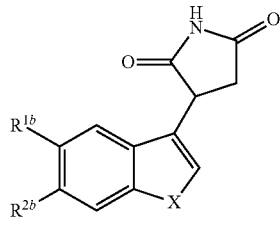

and pharmaceutically acceptable enantiomers, salts, solvates and prodrugs thereof, wherein:

X represents —$NQ^1$- or —$CQ^2=CQ^3$-, $Q^1$, $Q^2$ and $Q^3$ each independently represent H or alkyl; optionally, the alkyl is C1 to C6 alkyl, preferably $Q^1$, $Q^2$ and $Q^3$ each independently represent H or methyl, more preferably $Q^1$, $Q^2$ and $Q^3$ represent H, $R^{1b}$ and $R^{2b}$ each independently represent H, halo, cyano, alkyl or alkoxy, optionally, the alkyl is C1 to C6 alkyl and the alkoxy is C1 to C6 alkoxy, preferably $R^{1b}$ and $R^{2b}$ each independently represent H or halo;

under the condition that when X represents —$NQ^1$-, then $R^{1b}$ and $R^{2b}$ are not both H, and $R^{1b}$ and $R^{2b}$ are not both F, when X represents —$CQ^2=CQ^3$-, then $R^{1b}$ and $R^{2b}$ are not both H.

In another embodiment, $Q^1$ is H and X represents —$NH^1$— or —$CQ^2=CQ^3$-, $Q^2$ and $Q^3$ each independently represent H or alkyl; optionally, the alkyl is C1 to C6 alkyl, preferably $Q^2$ and $Q^3$ each independently represent H or methyl, more preferably $Q^2$ and $Q^3$ represent H, $R^{1b}$ and $R^{2b}$ each independently represent H, halo, cyano, alkyl or alkoxy, optionally, the alkyl is C1 to C6 alkyl and the alkoxy is C1 to C6 alkoxy, preferably $R^{1b}$ and $R^{2b}$ each independently represent H or halo;

under the condition that when X represents —NH—, then $R^{1b}$ and $R^{2b}$ are not both H, and $R^{1b}$ and $R^{2b}$ are not both F, when X represents —$CQ^2=CQ^3$-, then $R^{1b}$ and $R^{2b}$ are not both H.

Particularly preferred compounds of Formula I of the invention are those listed in Table 1 hereafter.

TABLE 1

| Cpd no | Structure | Chemical name |
|---|---|---|
| 1 | | 3-(5-fluoro-1H-indol-3-yl)pyrrolidine-2,5-dione |
| 1a | 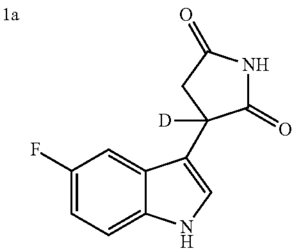 | (3-$^2$H)-3-(5-fluoro-1H-indol-3-yl)pyrrolidine-2,5-dione |
| 2 | 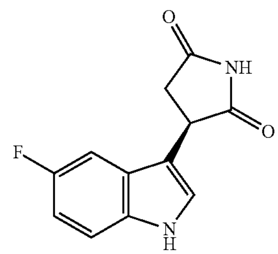 [SMILES: O=C1C[C@H](c2c[nH]c3ccc(F)cc23)C(=O)N1] | (−)-(R)-3-(5-fluoro-1H-indol-3-yl)pyrrolidine-2,5-dione |
| 3 | 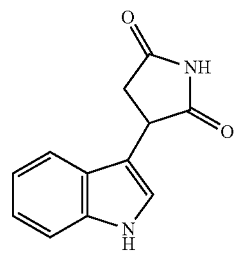 [SMILES: O=C1CC(c2c[nH]c3ccccc23)C(=O)N1] | 3-(1H-indol-3-yl)pyrrolidine-2,5-dione |
| 4 | 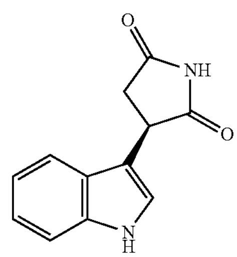 [SMILES: O=C1C[C@H](c2c[nH]c3ccccc23)C(=O)N1] | (−)-(R)-3-(1H-indol-3-yl)pyrrolidine-2,5-dione |
| 5 | 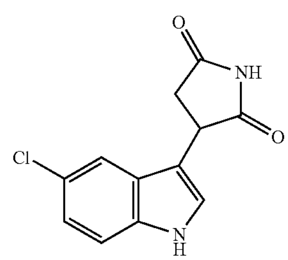 [SMILES: O=C1CC(c2c[nH]c3ccc(Cl)cc23)C(=O)N1] | 3-(5-chloro-1H-indol-3-yl)pyrrolidine-2,5-dione |
| 6 | 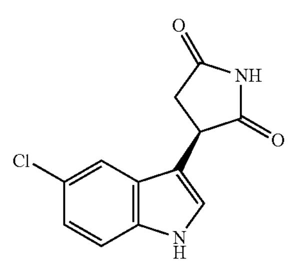 [SMILES: O=C1C[C@H](c2c[nH]c3ccc(Cl)cc23)C(=O)N1] | (−)-(R)-3-(5-chloro-1H-indol-3-yl)pyrrolidine-2,5-dione |

TABLE 1-continued

| Cpd no | Structure | Chemical name |
|---|---|---|
| 7 | 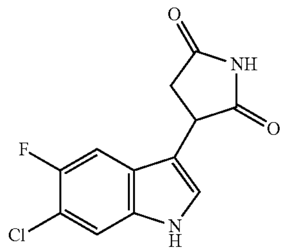 [SMILES: O=C1CC(c2c[nH]c3cc(Cl)c(F)cc23)C(=O)N1] | 3-(6-chloro-5-fluoro-1H-indol-3-yl)pyrrolidine-2,5-dione |
| 8 | 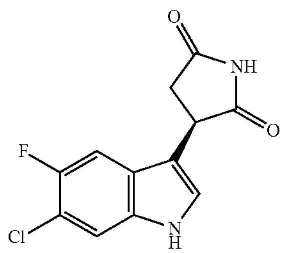 [SMILES: O=C1C[C@H](c2c[nH]c3cc(Cl)c(F)cc23)C(=O)N1] | (R)-3-(6-chloro-5-fluoro-1H-indol-3-yl)pyrrolidine-2,5-dione |
| 9 | 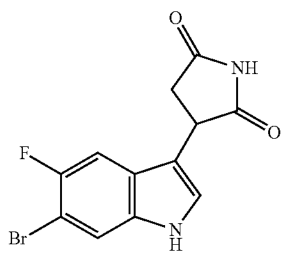 | 3-(6-bromo-5-fluoro-1H-indol-3-yl)pyrrolidine-2,5-dione |
| 10 | 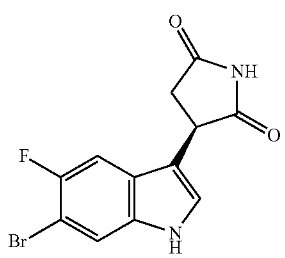 | (R)-3-(6-bromo-5-fluoro-1H-indol-3-yl)pyrrolidine-2,5-dione |
| 11 | 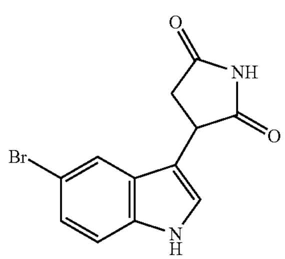 | 3-(5-bromo-1H-indol-3-yl)pyrrolidine-2,5-dione |
| 12 | 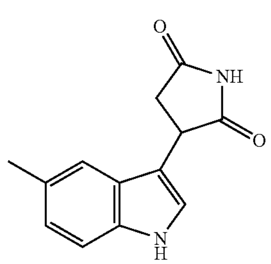 [SMILES: Cc1ccc2[nH]cc(C3CC(=O)NC3=O)c2c1] | 3-(5-methyl-1H-indol-3-yl)pyrrolidine-2,5-dione |
| 13 | | 3-(5-methoxy-1H-indol-3-yl)pyrrolidine-2,5-dione |
| 14 | | 3-(2,5-dioxopyrrolidin-3-yl)-1H-indole-5-carbonitrile |
| 15 | | 3-(5,6-difluoro-1H-indol-3-yl)pyrrolidine-2,5-dione |
| 16 | | 3-(5-fluoro-6-methyl-1H-indol-3-yl)pyrrolidine-2,5-dione |
| 17 | | 3-(6-fluoro-1H-indol-3-yl)pyrrolidine-2,5-dione |
| 18 | | 3-(6-chloro-1H-indol-3-yl)pyrrolidine-2,5-dione |

TABLE 1-continued

| Cpd no | Structure | Chemical name |
|---|---|---|
| 19 | 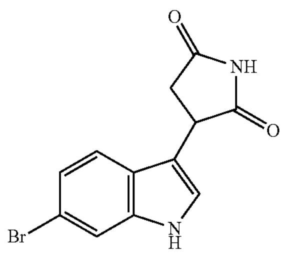 [SMILES: O=C1CC(c2c[nH]c3cc(Cl)ccc23)C(=O)N1] | 3-(6-bromo-1H-indol-3-yl)pyrrolidine-2,5-dione |
| 20 | 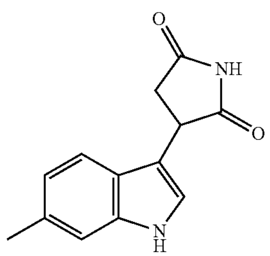 [SMILES: Cc1ccc2c(C3CC(=O)NC3=O)c[nH]c2c1] | 3-(6-methyl-1H-indol-3-yl)pyrrolidine-2,5-dione |
| 21 | 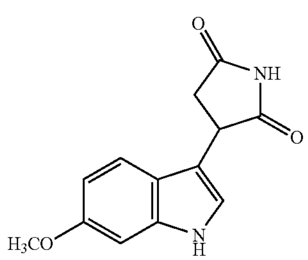 [SMILES: COc1ccc2c(C3CC(=O)NC3=O)c[nH]c2c1] | 3-(6-methoxy-1H-indol-3-yl)pyrrolidine-2,5-dione |
| 22 | 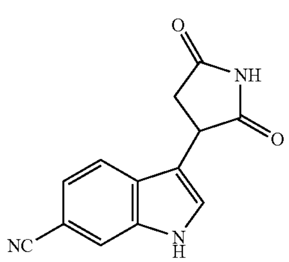 [SMILES: N#Cc1ccc2c(C3CC(=O)NC3=O)c[nH]c2c1] | 3-(2,5-dioxopyrrolidin-3-yl)-1H-indole-6-carbonitrile |
| 23 | 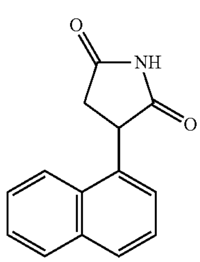 [SMILES: O=C1CC(c2cccc3ccccc23)C(=O)N1] | 3-(naphthalen-1-yl)pyrrolidine-2,5-dione |
| 24 | 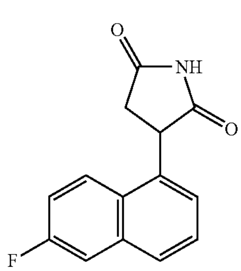 [SMILES: O=C1CC(c2cccc3cc(F)ccc23)C(=O)N1] | 3-(6-fluoronaphthalen-1-yl)pyrrolidine-2,5-dione |
| 25 | 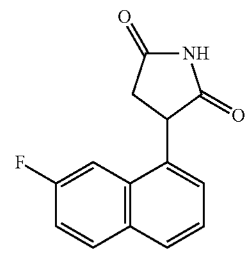 [SMILES: O=C1CC(c2cccc3ccc(F)cc23)C(=O)N1] | 3-(7-fluoronaphthalen-1-yl)pyrrolidine-2,5-dione |
| 26 | 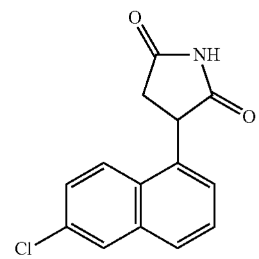 [SMILES: O=C1CC(c2cccc3cc(Cl)ccc23)C(=O)N1] | 3-(6-chloronaphthalen-1-yl)pyrrolidine-2,5-dione |
| 27 | | 3-(7-chloronaphthalen-1-yl)pyrrolidine-2,5-dione | or pharmaceutically acceptable enantiomers, salts, solvates and prodrugs thereof.

In Table 1, the term "Cpd" means compound.

The compounds of Table 1 were named using ChemBioDraw® Ultra version 12.0 (PerkinElmer).

According to a preferred embodiment, particularly preferred compounds of Formula I of the invention are compounds of Table 1 n° I, Ia, 2, 4, 6, 7, 8, 9, 10, 14, 16, 22, 24, 25, 26, 27.

The compounds of Formula I and subformulae thereof contain an asymmetric center and thus exist as different stereoisomeric forms. Accordingly, the present invention includes all possible stereoisomers and includes not only racemic compounds but the individual enantiomers and their non-racemic mixtures as well. When a compound is desired as a single enantiomer, such may be obtained by stereospecific synthesis, by resolution of the final product or any convenient intermediate, or by chiral chromatographic methods as each are known in the art. Resolution of the final product, an intermediate, or a starting material may be performed by any suitable method known in the art.

The compounds of the invention may be in the form of pharmaceutically acceptable salts. Pharmaceutically acceptable salts of the compounds of Formula I include base salts, which form non-toxic salts including, e.g., aluminum, calcium, choline, magnesium, potassium, sodium, zinc, and tetramethylammonium hydroxide. Although less desired, other bases may be selected, including, e.g., ammonia, ethylenediamine, N-methyl-glutamine, lysine, arginine, ornithine, N,N'-dibenzylethylene-diamine, chloroprocaine, diethanolamine, procaine, N-benzylphenethyl-amine, diethylamine, piperazine, tris(hydroxymethyl)aminomethane, benzathine, diethylamine, diolamine, glycine, lysine, meglumine, olamine, tromethamine, 2-(diethylamino)ethanol, ethanolamine, morpholine, and 4-(2-hydroxyethyl)morpholine. Hemisalts of bases may also be formed, for example, hemicalcium salts.

Pharmaceutically acceptable salts of compounds of Formula I may be prepared by one or more of these methods:
(i) by reacting the compound of Formula I and its subformulae with the desired base;
(ii) by removing an acid- or base-labile protecting group from a suitable precursor of the compound of Formula I (or its subformulae) or by ring-opening a suitable cyclic precursor, for example, a lactone or lactam, using the desired acid; or
(iii) by converting one salt of the compound of Formula I (or its subformulae) to another by reaction with an appropriate acid or by means of a suitable ion exchange column.

All these reactions are typically carried out in solution. The salt, may precipitate from solution and be collected by filtration or may be recovered by evaporation of the solvent. The degree of ionization in the salt may vary from completely ionized to almost non-ionized.

The compounds of the present invention may be administered in the form of pharmaceutically acceptable salts. The term "pharmaceutically acceptable salt" is intended to include all acceptable salts such as can be used as a dosage form for modifying the solubility or hydrolysis characteristics or can be used in sustained release or pro-drug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as, and tetramethylammonium hydroxide.

These salts may be prepared by standard procedures, e.g. by reacting a free acid with a suitable organic or inorganic base. Where a basic group is present, such as amino, an acidic salt, i.e. hydrochloride, hydrobromide, acetate, palmoate, and the like, can be used as the dosage form.

Also, in the case of an alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

All references to compounds of Formula I include references to enantiomers, salts, solvates, polymorphs, multicomponent complexes and liquid crystals thereof.

The compounds of the invention include compounds of Formula I as hereinbefore defined, including all polymorphs and crystal habits thereof, prodrugs and isomers thereof (including optical, geometric and tautomeric isomers) and isotopically-labeled compounds of Formula I.

In addition, although generally, with respect to the salts of the compounds of the invention, pharmaceutically acceptable salts are preferred, it should be noted that the invention in its broadest sense also included non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of Formula I above.

As used herein, the term "free base" refers to the non-salt form of a compound of Formula I.

Unless otherwise specified, reference to Formula I herein includes its subformulae, such as Formula Ia, Ib, Ia', I', I'', II, II', and II''.

The invention also generally covers all pharmaceutically acceptable predrugs and prodrugs of the compounds of Formula I.

Process for Manufacturing

The compounds of Formula I can be prepared by different ways with reactions known to a person skilled in the art.

The invention further relates to a first process for manufacturing of compounds of Formula I

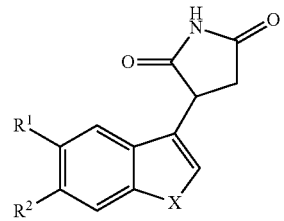

and pharmaceutically acceptable enantiomers, salts, solvates and prodrugs thereof, wherein X, $R^1$ and $R^2$ are as defined in Formula I;
comprising
reacting a compound of Formula (i)

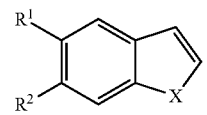

wherein X, $R^1$ and $R^2$ are as defined in Formula I
with maleimide to provide compound of Formula I;
and optionally separating enantiomers of Formula I' and I''.

According to one embodiment, the process may be performed in the presence of a suitable solvent such as but not limited to acetic acid, acetonitrile, DMSO, dichloroethane, DMF, water or mixtures thereof, preferably in acetic acid or acetonitrile. According to one embodiment, the process may be performed in the presence or absence of a suitable catalyst, such as but not limited to protic acids such as but not limited to acetic acid, hydrochloric acid or sulfuric acid; or Lewis acids such as but not limited to zinc chloride, zinc acetate, zinc triflate, aluminum chloride, cobalt chloride, cobalt acetate or iron chloride According to one embodiment, the process may be performed at a temperature ranging from 20° C. to about 200° C., preferably at a temperature ranging from 60° C. to 200° C., or about 150° C. to about 200° C., with or without microwave irradiation, for a period ranging from 10 minutes to a few hours, e.g. 10 minutes to 48 h.

According to one embodiment, the optional separation of the enantiomers of Formula I' and I'' starting from the corresponding compound of Formula I can be achieved by chiral HPLC, such as but not limited to using a Chiralpak® AS-H, Chiralcel® OJ-H or Chiralpak® IC column, using as eluents mixtures of appropriate solvents such as but not limited to supercritical $CO_2$, ethanol, methanol, hexane.

According to one embodiment, the optional separation of the enantiomers of Formula I' and I'' starting from the corresponding compound of Formula I can be achieved by resolution using optically pure acids, such as but not limited to camphosulfonic acid or tartaric acid, or with optically pure bases, such as but not limited to brucine, depending on the nature of the compound of Formula I.

The invention further relates to a second process of manufacturing of compounds of Formula I

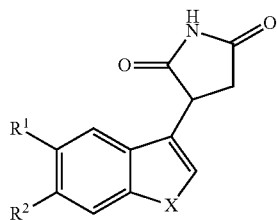

and pharmaceutically acceptable enantiomers, salts, solvates and prodrugs thereof, wherein X, $R^1$ and $R^2$ are as defined in Formula I;

comprising reacting a compound of Formula (ii)

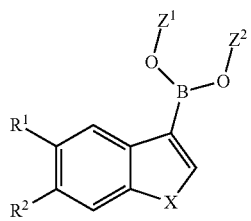

(ii)

wherein X, $R^1$ and $R^2$ are as defined in Formula I; and
$Z^1$ and $Z^2$ represent H or alkyl groups, with the possibility for $Z^1$ and $Z^2$ to form a ring;
with maleimide to provide compound of Formula
and optionally separating enantiomers of Formula I' and I''.

According to one embodiment, the process may be performed with or without a catalyst such as but not limited to [RhOH(cod)]$_2$.

According to one embodiment, the process may be performed in the presence of bases such as but not limited to trimethylamine (TEA), diethylisopropylamine (DIEA), sodium hydroxide (NaOH), potassium hydroxide (KOH), tripotassium phosphate ($K_3PO_4$), dipotassium carbonate ($K_2CO_3$), disodium carbonate ($Na_2CO_3$), preferably TEA or DIEA.

According to one embodiment, the process may be performed in the presence of a suitable solvent such as but not limited to dioxane, tetrahydrofuran (THF), dimethylformamide (DMF), water or mixtures thereof, preferably in dioxane or THF.

According to one embodiment, the process may be performed at a temperature ranging from 20° C. to about 150° C., with or without microwave irradiation, for a period ranging from 10 minutes to a few hours, e.g. 10 minutes to 24 h.

According to one embodiment, the optional separation of the enantiomers of Formula I' and I'' starting from the corresponding compound of Formula I can be achieved by chiral HPLC, such as but not limited to using a Chiralpak® AS-H, Chiralcel® OJ-H or Chiralpak® IC column, using as eluents mixtures of appropriate solvents such as but not limited to supercritical $CO_2$, ethanol, methanol, hexane.

According to one embodiment, the optional separation of the enantiomers of Formula I' and I'' starting from the corresponding compound of Formula I can be achieved by resolution using optically pure acids, such as but not limited to camphosulfonic acid or tartaric acid, or with optically pure bases, such as but not limited to brucine, depending on the nature of the compound of Formula I.

The invention further relates to a third process of manufacturing of compounds of Formula I

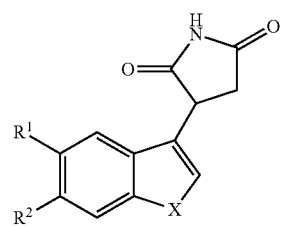

I and pharmaceutically acceptable enantiomers, salts, solvates and prodrugs thereof, wherein X, $R^1$ and $R^2$ are as defined in Formula I;
comprising
(a) reacting a compound of Formula (iii)

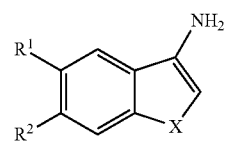

(iii)

wherein X, $R^1$ and $R^2$ are as defined in Formula I;
so as to obtain a compound of Formula (iv)

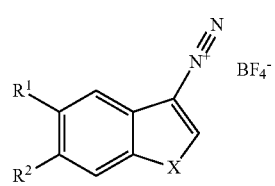

(iv)

wherein X, $R^1$ and $R^2$ are as defined in Formula I;
(b) reacting compound of Formula (iv) with maleic anhydride so as to obtain compound of Formula (v)

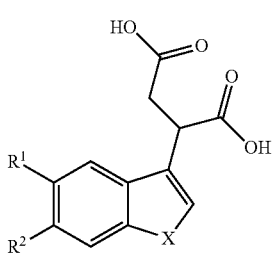

(v)

wherein X, $R^1$ and $R^2$ are as defined in Formula I;
and
(c) reacting compound of Formula (iv) with urea so as to obtain compound of Formula I
(d) optionally separating enantiomers of Formula I' and I''.

According to one embodiment, step (a) may be performed in the presence of a nitrite, such as but not limited to $NaNO_2$, $KNO_2$, tert-butyl nitrite or isoamyl nitrite.

According to one embodiment, step (a) may be performed in the presence of a suitable acid, such as but not limited to $HBF_4$.

According to one embodiment, step (a) may be performed in the presence of a suitable solvent such as but not limited to water.

According to one embodiment, step (a) may be performed at a temperature ranging from −20° C. to about 20° C., preferably at 0° C.

According to one embodiment, step (a) may be performed for a period ranging from 10 minutes and a few hours, e.g. 10 minutes to 24 h.

According to one embodiment, step (b) may be performed in the presence of a suitable catalyst, such as but not limited to $TiCl_3$.

According to one embodiment, step (b) may be performed in the presence of a suitable base, such as but not limited to NaOH or KOH.

According to one embodiment, step (b) may be performed in the presence of a suitable solvent such as but not limited to acetone, methyl ethyl ketone.

According to one embodiment, step (b) may be performed at a temperature ranging from −20° C. to about 20° C., preferably at 0° C.

According to one embodiment, step (b) may be performed for a period ranging from 10 minutes and a few hours, e.g. 10 minutes to 24 h.

According to one embodiment, step (c) may be performed in the absence or presence of a suitable solvent, at a temperature ranging from 100° C. to about 200° C., preferably at 180° C.

According to one embodiment, step (c) may be performed for a period ranging from 10 minutes and a few hours, e.g. 10 minutes to 24 h.

According to one embodiment, the optional separation of the enantiomers of Formula I' and I" starting from the corresponding compound of Formula I can be achieved by chiral HPLC, such as but not limited to using a Chiralpak® AS-H, Chiralcel® OJ-H or Chiralpak® IC column, using as eluents mixtures of appropriate solvents such as but not limited to supercritical $CO_2$, ethanol, methanol, hexane.

According to one embodiment, the optional separation of the enantiomers of Formula I' and I" starting from the corresponding compound of Formula I can be achieved by resolution using optically pure acids, such as but not limited to camphosulfonic acid or tartaric acid, or with optically pure bases, such as but not limited to brucine, depending on the nature of the compound of Formula I.

In general, the synthesis pathways for any individual compound of Formula I will depend on the specific substituents of each molecule and upon the ready availability of intermediates necessary; again such factors being appreciated by those of ordinary skill in the art.

According to a further general process, compounds of Formula I can be converted to alternative compounds of Formula I, employing suitable interconversion techniques well known by a person skilled in the art.

Compounds of the Formula I and related formulae can furthermore be obtained by liberating compounds of the Formula I from one of their functional derivatives by treatment with a solvolysing or hydrogenolysing agent.

Preferred starting materials for the solvolysis or hydrogenolysis are those which conform to the Formula I and related formulae, but contain corresponding protected amino and/or hydroxyl groups instead of one or more free amino and/or hydroxyl groups, preferably those which carry an amino-protecting group instead of an H atom bonded to an N atom, in particular those which carry an R*—N group, in which R* denotes an amino-protecting group, instead of an HN group, and/or those which carry a hydroxyl-protecting group instead of the H atom of a hydroxyl group, for example those which conform to the Formula I, but carry a —COOR group, in which R denotes a hydroxyl-protecting group, instead of a —COOH group.

It is also possible for a plurality of identical or different protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl, aralkanoyl, such as phenylacetyl, aroyl, such as benzoyl and tolyl, aryloxyalkanoyl, such as POA; alkoxycarbonyl, such as methoxycarbonyl, ethoxycarbonyl, 2,2,2-trichloroethoxycarbonyl, BOC (tert-butoxycarbonyl) and 2-iodoethoxycarbonyl, aralkoxycarbonyl, such as CBZ ("carbobenzoxy"), 4-methoxybenzyloxycarbonyl and FMOC, and arylsulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the Formula I and related formulae are liberated from their functional derivatives depending on the protecting group used for example strong inorganic acids, such as hydrochloric acid, perchloric acid or sulfuric acid, strong organic carboxylic acids, such as trichloroacetic acid, TFA or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as THF or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. Trifluoracetic acid (TFA) is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature).

The BOC, OtBu and Mtr groups can, for example, preferably be cleaved off using TFA in dichloromethane or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Examples of suitable inert solvents are hydrocarbons, such as hexane, petroleum ether, benzene, toluene or xylene, chlorinated hydrocarbons, such as trichloroethylene, 1,2-dichloroethane, tetrachloromethane, trifluoromethylbenzene, chloroform or dichloromethane, alcohols, such as methanol, ethanol, isopropanol, n-propanol, n-butanol or tert-butanol, ethers, such as diethyl ether, diisopropyl ether, tetrahydrofuran (THF) or dioxane, glycol ethers, such as ethylene glycol monomethyl or monoethyl ether or ethylene glycol dimethyl ether (diglyme), ketones, such as acetone or butanone, amides, such as acetamide, dimethylacetamide, N-methylpyrrolidone (NMP) or dimethylformamide (DMF), nitriles, such as acetonitrile, sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be hydrolysed, for example, using HCl, $H_2SO_4$, or using LiOH, NaOH or KOH in water, water/THF, water/THF/ethanol or water/dioxane, at temperatures between 0 and 100° C.

Free amino groups can furthermore be acylated in a conventional manner using an acyl chloride or anhydride or alkylated using an unsubstituted or substituted alkyl halide, advantageously in an inert solvent, such as dichloromethane or THF and/or in the presence of a base, such as triethylamine or pyridine, at temperatures between −60° C. and +30° C.

For all the protection and deprotection methods, see Philip J. Kocienski, in "Protecting Groups", Georg Thieme Verlag Stuttgart, N.Y., 1994 and, Theodora W. Greene and Peter G. M. Wuts in "Protective Groups in Organic Synthesis", Wiley Interscience, 3rd Edition 1999.

Reaction schemes as described in the example section are illustrative only and should not be construed as limiting the invention in any way.

Uses

The invention is further directed to a medicament comprising at least one compound of the invention, or a pharmaceutically acceptable enantiomer, salt, solvate and prodrug thereof, or a deuterated form thereof, as active ingredient.

In the present invention, the expression "compound of the invention" encompasses compounds of Formula I and its subformulae, or a pharmaceutically acceptable enantiomer, salt, solvate and prodrug thereof, or a deuterated form thereof. Examples are identified in Table 1 and in the examples. Illustrative compounds include:
3-(5-fluoro-1H-indol-3-yl)pyrrolidine-2,5-dione,
(−)-(R)-3-(5-fluoro-1H-indol-3-yl)pyrrolidine-2,5-dione,
(+)-(S)-3-(5-fluoro-1H-indol-3-yl)pyrrolidine-2,5-dione,
3-(1H-indol-3-yl)pyrrolidine-2,5-dione,
(−)-(R)-3-(1H-indol-3-yl)pyrrolidine-2,5-dione,
(+−)-(S)-3-(1H-indol-3-yl)pyrrolidine-2,5-dione,
3-(5-chloro-1H-indol-3-yl)pyrrolidine-2,5-dione,
(−)-(R)-3-(5-chloro-1H-indol-3-yl)pyrrolidine-2,5-dione,
(+)-(S)-3-(5-chloro-1H-indol-3-yl)pyrrolidine-2,5-dione,
3-(6-chloro-5-fluoro-1H-indol-3-yl)pyrrolidine-2,5-dione,
(R)-3-(6-chloro-5-fluoro-1H-indol-3-yl)pyrrolidine-2,5-dione,
(S)-3-(6-chloro-5-fluoro-1H-indol-3-yl)pyrrolidine-2,5-dione,
3-(6-bromo-5-fluoro-1H-indol-3-yl)pyrrolidine-2,5-dione,
(R)-3-(6-bromo-5-fluoro-1H-indol-3-yl)pyrrolidine-2,5-dione,
(S)-3-(6-bromo-5-fluoro-1H-indol-3-yl)pyrrolidine-2,5-dione,
3-(5-bromo-1H-indol-3-yl)pyrrolidine-2,5-dione,
3-(5-methyl-1H-indol-3-yl)pyrrolidine-2,5-dione,
3-(5-methoxy-1H-indol-3-yl)pyrrolidine-2,5-dione,
3-(2,5-dioxopyrrolidin-3-yl)-1H-indole-5-carbonitrile,
3-(5,6-difluoro-1H-indol-3-yl)pyrrolidine-2,5-dione,
3-(5-fluoro-6-methyl-1H-indol-3-yl)pyrrolidine-2,5-dione,
3-(6-fluoro-1H-indol-3-yl)pyrrolidine-2,5-dione,
3-(6-chloro-1H-indol-3-yl)pyrrolidine-2,5-dione,
3-(6-bromo-1H-indol-3-yl)pyrrolidine-2,5-dione,
3-(6-methyl-1H-indol-3-yl)pyrrolidine-2,5-dione,
3-(6-methoxy-1H-indol-3-yl)pyrrolidine-2,5-dione,
3-(2,5-dioxopyrrolidin-3-yl)-1H-indole-6-carbonitrile,
3-(naphthalen-1-yl)pyrrolidine-2,5-dione,
3-(6-fluoronaphthalen-1-yl)pyrrolidine-2,5-dione,
3-(7-fluoronaphthalen-1-yl)pyrrolidine-2,5-dione,
3-(6-chloronaphthalen-1-yl)pyrrolidine-2,5-dione, and
3-(7-chloronaphthalen-1-yl)pyrrolidine-2,5-dione.

Optionally, these compounds of Formula I may be deuterated, e.g., at the chiral center. An illustrated deuterated compound is (3-$^2$H)-3-(5-fluoro-1H-indol-3-yl)pyrrolidine-2,5-dione.

In one embodiment, the compound has the structure of Formula II:

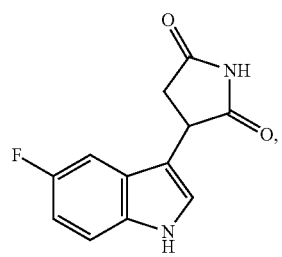

II or a pharmaceutically acceptable salt thereof. The compound may be a racemate, wherein each stereoisomer is present an amount of about 50 mol % (48% to 52%). Alternatively or additionally, a separate enantiomer of the compound is used in a pharmaceutical composition. In one embodiment, the enantiomer is characterized by structure of Formula II':

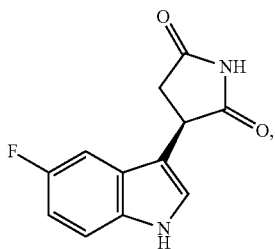

II' which is present in free base (not salt) form. Optionally, the compound is present as a pharmaceutically acceptable salt or solvate thereof. In another embodiment, the (S)-enantiomer is additionally or alternatively present in the composition. This enantiomer is characterized by the structure of Formula II":

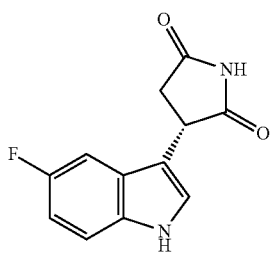

II"

which is in free base form, or optionally may be salt form. Pharmaceutical compositions may contain mixtures of the compounds of Formula II' and Formula II". A variety of ratios of the two compounds may be selected. For example, the ratio may be about 1:1, or the compound of Formula II' may be present in greater than 50%, greater than 95%, greater than 90%, or about 95% to 100%. Similarly, in other compositions, the compound of Formula II" may be present in greater than 50%. The discussion of suitable ratios and molar percentages of enantiomers relating to the compounds of Formula I and its subformulae earlier to in the specification, is hereby incorporated by reference.

The invention also provides pharmaceutical compositions comprising a compound of the invention or a pharmaceutically acceptable enantiomer, salt, solvate and prodrug thereof and at least one pharmaceutically acceptable carrier, diluent, excipient and/or adjuvant. The carrier(s) are "acceptable" in the sense of being compatible with the other ingredients of the formulation and, in the case of a pharmaceutically acceptable carrier, not deleterious to the recipient thereof in an amount used in the medicament.

According to one embodiment, the invention also covers pharmaceutical compositions which contain, in addition to a compound of the present invention or a pharmaceutically acceptable enantiomer, salt, solvate and prodrug thereof as active ingredient, additional therapeutic agents and/or active ingredients.

By means of non-limiting examples, the compounds of the invention may be formulated as a pharmaceutical preparation in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use.

Depending on the condition to be prevented or treated and the route of administration, the active compound of the invention may be administered as a single daily dose, divided over one or more daily doses, or essentially continuously, e.g. using a drip infusion.

The invention also relates to the use of compounds of the invention, or pharmaceutically acceptable enantiomers, salts, solvates and prodrugs thereof, in the treatment and/or prevention of cancer and endometriosis. In one embodiment, the invention relates to the use of compounds of the invention, or pharmaceutically acceptable enantiomers, salts, solvates and prodrugs thereof, in the treatment and/or prevention of cancer. In another embodiment, the invention relates to the use of compounds of the invention, or pharmaceutically acceptable enantiomers, salts, solvates and prodrugs thereof, in the treatment and/or prevention of endometriosis.

In one embodiment, compounds of the invention or pharmaceutically acceptable enantiomers, salts, solvates or prodrugs thereof are for use in the treatment and/or prevention of cancer and endometriosis. According to one embodiment, compounds of the invention, or pharmaceutically acceptable enantiomers, salts, solvates and prodrugs thereof, are for use in the treatment and/or prevention of cancer. According to another embodiment, compounds of the invention, or pharmaceutically acceptable enantiomers, salts, solvates and prodrugs thereof, are for use in the treatment and/or prevention of endometriosis.

The invention further relates to a method for treatment or prevention of cancer and endometriosis, which comprises administering to a subject in need thereof a therapeutically effective amount of the compound according to the invention or a pharmaceutically acceptable enantiomers, salts, solvates or prodrugs thereof. In one embodiment, the invention relates to a method for treatment or prevention of cancer, which comprises administering to a subject in need thereof a therapeutically effective amount of the compound according to the invention or a pharmaceutically acceptable enantiomers, salts, solvates or prodrugs thereof. In another embodiment, the invention relates to a method for treatment or prevention of endometriosis, which comprises administering to a subject in need thereof a therapeutically effective amount of the compound according to the invention or a pharmaceutically acceptable enantiomers, salts, solvates or prodrugs thereof.

In one embodiment, compounds of the invention or pharmaceutically acceptable enantiomers, salts, solvates or prodrugs thereof are for use in increasing immune recognition and destruction of the cancer cells.

The compounds of the invention are therefore useful as medicaments, in particular in the prevention and/or treatment of cancer.

The invention further provides the use of a compound according to the invention or a pharmaceutically acceptable enantiomer, salt, solvate and prodrug thereof for the manufacture of a medicament for treating and/or preventing cancer.

Various cancers are known in the art. The cancer may be metastatic or non-metastatic. The cancer may be may be familial or sporadic. In some embodiments, the cancer is selected from the group consisting of: leukemia and multiple myeloma. In one embodiment, the cancer is leukemia. In one embodiment, the cancer is multiple myeloma.

Additional cancers that can be treated using the methods of the invention include, for example, benign and malignant solid tumors and benign and malignant non-solid tumors. In one embodiment, the cancer is benign solid tumors. In one embodiment, the cancer is malignant solid tumors. In one embodiment, the cancer is benign non-solid tumors. In one embodiment, the cancer is malignant non-solid tumors.

Examples of solid tumors include, but are not limited to: biliary tract cancer, brain cancer (including glioblastomas and medulloblastomas), breast cancer, cervical cancer, choriocarcinoma, colon cancer, endometrial cancer, esophageal cancer, gastric cancer, intraepithelial neoplasms (including Bowen's disease and Paget's disease), liver cancer, lung cancer, neuroblastomas, oral cancer (including squamous cell carcinoma), ovarian cancer (including those arising from epithelial cells, stromal cells, germ cells and mesenchymal cells), pancreatic cancer, prostate cancer, rectal cancer, renal cancer (including adenocarcinoma and Wilms tumour), sarcomas (including leiomyosarcoma, rhabdomyosarcoma, liposarcoma, fibrosarcoma and osteosarcoma), skin cancer (including melanoma, Kaposi's sarcoma, basocellular cancer and squamous cell cancer), testicular cancer including germinal tumors (seminomas, and non-seminomas such as teratomas and choriocarcinomas), stromal tumors, germ cell tumors, and thyroid cancer (including thyroid adenocarcinoma and medullary carcinoma).

In one embodiment, the cancer is biliary tract cancer. In one embodiment, the cancer is brain cancer, including glioblastomas and medulloblastomas. In one embodiment, the cancer is breast cancer. In one embodiment, the cancer is cervical cancer. In one embodiment, the cancer is choriocarcinoma. In one embodiment, the cancer is colon cancer. In one embodiment, the cancer is endometrial cancer. In one embodiment, the cancer is esophageal cancer. In one embodiment, the cancer is gastric cancer. In one embodiment, the cancer is intraepithelial neoplasms, including Bowen's disease and Paget's disease. In one embodiment, the cancer is liver cancer. In one embodiment, the cancer is lung cancer. In one embodiment, the cancer is neuroblastomas. In one embodiment, the cancer is oral cancer, including squamous cell carcinoma. In one embodiment, the cancer is ovarian cancer, including those arising from epithelial cells, stromal cells, germ cells and mesenchymal cells. In one embodiment, the cancer is pancreatic cancer. In one embodiment, the cancer is prostate cancer. In one embodiment, the cancer is rectal cancer. In one embodiment, the cancer is renal cancer, including adenocarcinoma and Wilms tumour. In one embodiment, the cancer is sarcomas, including leiomyosarcoma, rhabdomyosarcoma, liposarcoma, fibrosarcoma and osteosarcoma. In one embodiment, the cancer is skin cancer, including melanoma, Kaposi's sarcoma, basocellular cancer and squamous cell cancer. In one embodiment, the cancer is testicular cancer including germinal tumors (seminomas, and non-seminomas such as teratomas and choriocarcinomas). In one embodiment, the cancer is stromal tumors. In one embodiment, the cancer is germ cell tumors. In one embodiment, the cancer is thyroid cancer, including thyroid adenocarcinoma and medullary carcinoma.

Examples of non-solid tumors include but are not limited to hematological neoplasms. As used herein, a hematologic neoplasm is a term of art which includes lymphoid disorders, myeloid disorders, and AIDS associated leukemias.

Lymphoid disorders include but are not limited to acute lymphocytic leukemia and chronic lymphoproliferative disorders (e.g., lymphomas, myelomas, and chronic lymphoid leukemias). Lymphomas include, for example, Hodgkin's disease, non-Hodgkin's lymphoma lymphomas, and lymphocytic lymphomas). Chronic lymphoid leukemias include, for example, T cell chronic lymphoid leukemias and B cell chronic lymphoid leukemias.

In one embodiment, the lymphoid disorder is acute lymphocytic leukemia. In one embodiment, the lymphoid disorder is chronic lymphoproliferative disorders (e.g., lymphomas, myelomas, and chronic lymphoid leukemias). In one embodiment, the lymphoma is Hodgkin's disease. In one embodiment, the lymphoma is non-Hodgkin's lymphoma. In one embodiment, the lymphoma is lymphocytic lymphoma. In one embodiment, the chronic lymphoid leukemia is T cell chronic lymphoid leukemia. In one embodiment, the chronic lymphoid leukemia is B cell chronic lymphoid leukemia.

The invention also provides for a method for delaying in a subject the onset of cancer comprising the administration of a pharmaceutically effective amount of a compound according to the invention or pharmaceutically acceptable enantiomer, salt, solvate and prodrug thereof to a subject in need thereof.

The invention is further directed to the use of compounds of the invention, or pharmaceutically acceptable enantiomers, salts, solvates and prodrugs thereof as IDO1 inhibitors.

Accordingly, in a particularly preferred embodiment, the invention relates to the use of compounds of Formula I and subformulae in particular those of Table 1 above, or pharmaceutically acceptable enantiomers, salts, solvates and prodrugs thereof, as IDO1 inhibitors.

Accordingly, in another aspect, the invention relates to the use of these compounds or enantiomers, salts, solvates and prodrugs thereof for the synthesis of IDO1 inhibitors.

According to a further feature of the present invention there is provided a method for modulating IDO1 activity, in a subject in need of such treatment, which comprises administering to said subject an effective amount of compound of the present invention, or a pharmaceutically acceptable enantiomer, salt, solvate and prodrug thereof.

According to a further feature of the present invention there is provided the use of a compound of the invention or a pharmaceutically acceptable enantiomer, salt, solvate and prodrug thereof for the manufacture of a medicament for modulating IDO1 activity in a subject in need of such treatment, which comprises administering to said subject an effective amount of compound of the present invention, or a pharmaceutically acceptable enantiomer, salt, solvate and prodrug thereof.

Definitions

In the present invention, the following terms have the following meanings:

Where groups may be substituted, such groups may be substituted with one or more substituents, and preferably with one, two or three substituents.

Substituents may be selected from but not limited to, for example, the group comprising halogen, hydroxyl, oxo, nitro, amido, carboxy, amino, cyano, haloalkoxy, and haloalkyl.

The term "halogen" or "halo" means fluoro (F), chloro (Cl), bromo (Br), or iodo (I). Preferred halo groups are fluoro and chloro.

The term "alkyl" by itself or as part of another substituent refers to a hydrocarbyl radical of Formula $C_nH_{2n+1}$ wherein n is a number greater than or equal to 1. Generally, alkyl groups of this invention comprise from 1 to 6 carbon atoms (C1, C2, C3, C4, C5, or C6 carbons, inclusive), preferably from 1 to 4 carbon atoms, more preferably from 1 to 3 carbon atoms. Alkyl groups may be linear or branched and may be substituted as indicated herein. Suitable alkyl groups include methyl, ethyl, n-propyl, i-propyl, n-butyl, i-butyl, s-butyl and t-butyl, pentyl and its isomers (e.g. n-pentyl, iso-pentyl), and hexyl and its isomers (e.g. n-hexyl, iso-hexyl). Optionally, an alkyl may be substituted with 1, 2 or 3 substituents. Such a substituent may be a hydroxy, amino-, halogen, or C1-C3 alkyl group. In one embodiment, a halogen substituent is a F or Br. In another embodiment, an alkyl substituent is a methyl group. The term "alkoxy" refers to any group O-alkyl.

The term "amino" refers to a —$NH_2$ group or any group derived thereof by substitution of one nor two hydrogen atom by an organic aliphatic or aromatic group. Preferably, groups derived from —$NH_2$ are "alkylamino" groups, i.e. N-alkyl groups, comprising monoalkylamino and dialkylamino. According to a specific embodiment, the term "amino" refers to $NH_2$, NHMe or $NMe_2$.

The term "amino-protecting group" refers to a protecting group for an amine function. According to a preferred embodiment, the amino-protecting group is selected in the groups comprising: arylsulphonyl, tert-butoxy carbonyl, methoxymethyl, para-methoxy benzyl or benzyl.

The term "solvate" is used herein to describe a compound in this invention that contains stoichiometric or sub-stoichiometric amounts of one or more pharmaceutically acceptable solvent molecule such as ethanol. The term "hydrate" refers to when the said solvent is water.

The compounds of the invention include compounds of Formula I as hereinbefore defined, including all polymorphs and crystal habits thereof, prodrugs and prodrugs thereof and isotopically-labeled compounds of Formula I.

The invention also generally covers all pharmaceutically acceptable predrugs and prodrugs of the compounds of Formula I.

The term "prodrug" as used herein means the pharmacologically acceptable derivatives of compounds of Formula I, such as for example amides, whose in vivo biotransformation product generates the biologically active drug. Prodrugs are generally characterized by increased bio-availability and are readily metabolized into biologically active compounds in vivo.

The term "predrug", as used herein, means any compound that will be modified to form a drug species, wherein the modification may take place either inside or outside of the body, and either before or after the predrug reaches the area of the body where administration of the drug is indicated.

The term "subject" refers to a mammal, preferably a human. In one embodiment, a subject may be a "patient", i.e. a warm-blooded animal, more preferably a human, who/which is awaiting the receipt of, or is receiving medical care or was/is/will be the object of a medical procedure, or is monitored for the development of a disease.

The term "human" refers to a person of both genders and at any stage of development (i.e. neonate, infant, juvenile, adolescent, adult).

The terms "treat", "treating" and "treatment", as used herein, are meant to include alleviating, attenuating or abrogating a condition or disease and/or its attendant symptoms.

The terms "prevent", "preventing" and "prevention", as used herein, refer to a method of delaying or precluding the onset of a condition or disease and/or its attendant symptoms, barring a subject from acquiring a condition or disease, or reducing a subject's risk of acquiring a condition or disease.

The term "therapeutically effective amount" (or more simply an "effective amount") as used herein means the amount of active agent or active ingredient that is sufficient to achieve the desired therapeutic or prophylactic effect in the subject to which/whom it is administered.

The term "administration", or a variant thereof (e.g. "administering"), means providing the active agent or active ingredient, alone or as part of a pharmaceutically acceptable composition, to the subject in whom/which the condition, symptom, or disease is to be treated or prevented.

By "pharmaceutically acceptable" is meant that the ingredients of a pharmaceutical composition are compatible with each other and not deleterious to the subject to which it is administered.

The term "inhibitor" refers to a natural or synthetic compound that has a biological effect to inhibit or significantly reduce or down-regulate the expression of a gene and/or a protein or that has a biological effect to inhibit or significantly reduce the biological activity of a protein. Consequently, an "IDO1 inhibitor" refers to a compound that has a biological effect to inhibit or significantly reduce or down-regulate the expression of the gene encoding for IDO1 and/or the expression of IDO1 and/or the biological activity of IDO1.

"D" and "d" both refer to deuterium. "dx.y" refers to substitution with from x to y number of deuterium atoms.

"Stereoisomer" refers to both enantiomers and diastereomers. A group is "substituted with" a substituent when one or more hydrogen atoms of the group are replaced with a corresponding number of substituent atoms (if the substituent is an atom) or groups (if the substituent is a group). For example, "substituted with deuterium" refers to the replacement of one or more hydrogen atoms with a corresponding number of deuterium atoms.

The words "comprise", "comprises", and "comprising" are to be interpreted inclusively rather than exclusively. The works "consist", "consisting", and its variants, are to be interpreted exclusively, rather than inclusively.

As used herein, the term "about" means a variability of 10% from the reference given, unless otherwise specified.

EXAMPLES

The present invention will be better understood with reference to the following examples. These examples are intended to representative of specific embodiments of the invention, and are not intended as limiting the scope of the invention.

I. Chemistry Examples

The MS data provided in the examples described below were obtained as followed: Mass spectrum: LC/MS Agilent 6110 (ESI) or a Waters Acquity SQD (ESI)

The NMR data provided in the examples described below were obtained as followed: Bruker Ultrashield™ 400 PLUS and Bruker Fourier 300 MHz and TMS was used as an internal standard.

The microwave chemistry was performed on a single mode microwave reactor Initiator Microwave System EU from Biotage.

Preparative HPLC purifications were performed with a mass directed autopurification Fractionlynx from Waters equipped with a Xbridge™ Prep C18 OBD column 19×150 mm 5 μm, unless otherwise reported. All HPLC purifications were performed with a gradient of $CH_3CN/H_2O/NH_4HCO_3$ (5 mM), $CH_3CN/H_2O$/TFA (0.1%), or $CH_3CN/H_2O$/ $NH_3H_2O$ (0.1%).

Compound 1:
3-(5-fluoro-1H-indol-3-yl)pyrrolidine-2,5-dione

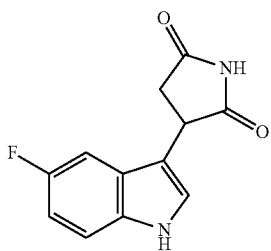 [SMILES: O=C1CC(c2c[nH]c3ccc(F)cc23)C(=O)N1]

A. Route A

A mixture of 5-fluoro-1H-indole (300 mg; 2.22 mmol), maleimide (646 mg; 6.65 mmol) in AcOH (2 mL) was stirred at 170° C. for 2 h in a microwave reaction. The reaction mixture was concentrated in vacuo. The residue was neutralized with saturated aqueous $NaHCO_3$ solution to pH 7-8 and extracted with EtOAc (10 mL×3). The combined organic layers were dried over anhydrous $Na_2SO_4$, filtered, concentrated, and purified by preparative HPLC to afford 180 mg (35%) of the title compound as a yellow solid. LC-MS for $C_{12}H_9FN_2O_2$—H⁻ [M–H]: calcd. 231.1. found: 231.0. ¹H NMR (300 MHz, DMSO-$d_6$) δ [ppm]: 11.30 (brs, 1H), 11.14 (s, 1H), 7.41 (d, J=2.5 Hz, 1H), 7.36 (dd, J=9.0, 4.6 Hz, 1H), 7.20 (dd, J=10.1, 2.5 Hz, 1H), 6.94 (ddd, J=9.2, 9.0, 2.5 Hz, 1H), 4.33 (dd, J=9.5, 5.5 Hz, 1H), 3.17 (dd, J=18.0, 9.5 Hz, 1H), 2.79 (dd, J=18.0, 5.5 Hz, 1H).

Route B

Alternatively, a mixture of 5-Fluoroindole (5.00 g, 5.00 g, 35.5 mmol, 96 mass %, 1.00) and Maleimide (1.5 equiv., 5.17 g, 53.3 mmol, 1.50) was charged in a 50 mL vessel, and then Acetonitrile (3 L/kg, 15.0 mL, 11.7 g, 286 mmol, 100 mass %) and Zinc Chloride (1.05 equiv., 5.08 g, 37.3 mmol, 100 mass %) were added. The reaction was heated to 85° C. over 10 min and then maintained at 85° C. for 24 hrs. While still at 85° C., Water (6 L/kg, 30.0 mL, 30.0 g, 1670 mmol, 100 mass %) was added slowly, while maintaining the temperature above 80° C.

Yellow solids precipitated. The reaction mixture was cooled to 50° C. over 1 hour followed by stirring at 50° C. for 2 hours, then cooled 10° C. over 1 hour. The reaction was stirred at 10° C. for 1 hour. The solids were filtered off, then the filter cake was washed 2 times with 5 ml 1:1 ACN/water to afford isolated compound (6.85 g, 6.85 g, 29.5 mmol, 83.1% Yield).

For purification, the resulting isolated compound was charged (6.85 g, 6.85 g, 29.5 mmol, 100 mass %) into a vessel, followed by addition of Tetrahydrofuran (6 L/kg, 41.1 mL, 36.4 g, 505 mmol, 100 mass %). This mixture was heated to 66° C. to form a homogeneous solution. Heptane (4 L/kg, 27.4 mL, 18.7 g, 187 mmol, 100 mass %, was added slowly at 66° C. solids began to precipitate after 5 volumes. The mixture was cooled to 25° C. over 3 hours, then filtered and washed with heptane, followed by drying in the high vacuum oven overnight. Isolated compound (4.93 g, 4.93 g, 21.2 mmol, 100 mass %, 72.0% Yield).

This isolated compound is charged 2 (1.00 g, 4.3 mmol, 100 mass %,) into a 50 ml vessel And Tetrahydrofuran (6 L/kg, 6 mL, 100 mass %) and Heptane (6 L/kg, 6 mL, 100 mass %) were added. The slurry was stirred at 25° C. for 48 hrs. The solids were filtered off and dried in the high vacuum oven overnight. The Isolated compound: (0.89 g, 0.89 g, 3.83 mmol, 100 mass %, 89.00% Yield).

Compound 1a: (3-²H)-3-(5-fluoro-1H-indol-3-yl) pyrrolidine-2,5-dione

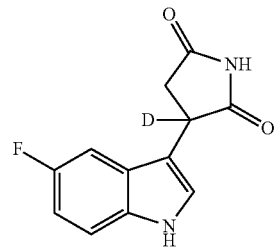 [SMILES: [2H]C1(c2c[nH]c3ccc(F)cc23)CC(=O)NC1=O]

To a solution of 3-(5-Fluoro-1H-indol-3-yl)-pyrrolidine-2,5-dione (Compound 1, 200 mg, 0.87 mmol) in $D_2O$ (3 mL) was added $K_2CO_3$ (300 mg, 2.2 mmol). The reaction was stirred at 40° C. overnight. The mixture was extracted with EtOAc. The organic layer was dried, filtered, concentrated and purified by preparative HPLC to afford the Title Compound (20 mg, 10%) as a yellow solid. LC-MS for $C_{12}H_6DFN_2O_2$—H⁻ [M–H]⁻: calcd. 232.1. found: 232.1. ¹H NMR (300 MHz, DMSO-$d_6$) δ [ppm]: 11.28 (s, 1H), 11.15 (s, 1H), 7.41 (d, J=2.1 Hz, 1H), 7.36 (dd, J=8.7, 4.5 Hz, 1H), 7.20 (dd, J=10.2, 2.4 Hz, 1H), 6.97-6.90 (m, 1H), 3.19-3.13 (m, 1H), 2.80-2.74 (m, 1H).

Compound 2: (−)-(R)-3-(5-fluoro-1H-indol-3-yl)pyrrolidine-2,5-dione

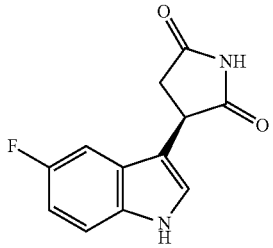 [SMILES: O=C1C[C@H](c2c[nH]c3ccc(F)cc23)C(=O)N1]

50 mg of the title compound was obtained as a yellow solid by chiral preparative HPLC separation of 150 mg of compound 1. Preparative chiral HPLC: Chiralpak® AS-H 250 mm×20 mm 5 µm, Mobile phase: $CO_2$/IPA=60/40; Flow: 50 mL/min 214 nm ambient temperature. Analytical chiral HPLC: Chiralpak® IC 250 mm×4.6 mm 5 µm, Mobile phase: Hexane/EtOH=70/30; Flow: 1.0 mL/min 230 nm ambient temperature; Retention time: 6.25 min. P1: 96.3% e.e. $[\alpha]^{254}_D = -75.4$ (c=0.0014, MeOH). LC-MS for $C_{12}H_9FN_2O_2$+H⁺ [M+H]⁺: calcd. 233.1. found: 233.1. ¹H NMR (300 MHz, DMSO-$d_6$) δ [ppm]: 11.30 (brs, 1H), 11.14 (s, 1H), 7.41 (d, J=2.5 Hz, 1H), 7.36 (dd, J=9.0, 4.6 Hz, 1H), 7.20 (dd, J=10.1, 2.5 Hz, 1H), 6.94 (ddd, J=9.2, 9.0, 2.5 Hz, 1H), 4.33 (dd, J=9.5, 5.5 Hz, 1H), 3.17 (dd, J=18.0, 9.5 Hz, 1H), 2.79 (dd, J=18.0, 5.5 Hz, 1H).

Compound 2a: (+)-(S)-3-(5-fluoro-1H-indol-3-yl)pyrrolidine-2,5-dione

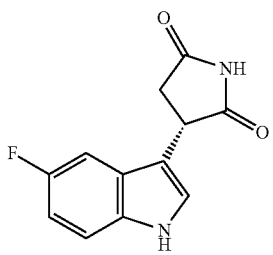 [SMILES: O=C1C[C@@H](c2c[nH]c3ccc(F)cc23)C(=O)N1]

Isolated as second-eluting enantiomer from the chiral separation described for Compound 2a. Chiral HPLC retention time: 6.96 min. 98.5% e.e. $[G]254_D=70$ (c=0.0014, MeOH).

Compound 3: 3-(1H-indol-3-yl)pyrrolidine-2,5-dione

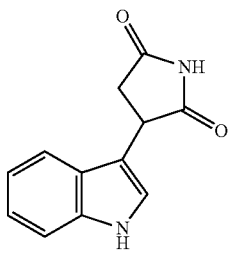 [SMILES: O=C1CC(c2c[nH]c3ccccc23)C(=O)N1]

Following the general method as outlined for compound 1, starting from 1H-indole (2.00 g; 17.1 mmol) and maleimide (4.96 g; 51.1 mmol), 2.50 g (68%) of the title compound was obtained as a yellow solid after purification by silica gel chromatography (petroleum ether/EtOAc=1/1). LC-MS for $C_{12}H_{10}FN_2O_2$+H⁺[M+H]⁺: calcd. 215.1. found: 215.1. ¹H NMR (400 MHz, DMSO-$d_6$) δ [ppm]: 11.29 (s, 1H), 11.02 (s, 1H), 7.42 (d, J=8.0 Hz, 1H), 7.39 (d, J=8.1 Hz, 1H), 7.32 (d, J=2.4 Hz, 1H), 7.12-7.07 (m, 1H), 7.02-6.97 (m, 1H), 4.33 (dd, J=9.5, 5.3 Hz, 1H), 3.18 (dd, J=18.0, 9.5 Hz, 1H), 2.76 (dd, J=18.0, 5.3 Hz, 1H).

Compound 4: (−)-(R)-3-(1H-indol-3-yl)pyrrolidine-2,5-dione

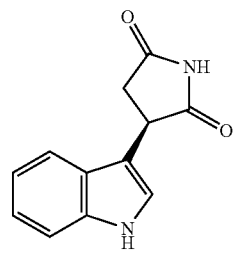 [SMILES: O=C1C[C@H](c2c[nH]c3ccccc23)C(=O)N1]

100 mg of the title compound was obtained as a yellow solid by chiral preparative HPLC separation of 250 mg of compound 3. Preparative chiral HPLC: Chiralcel OJ-H 250 mm×4.6 mm 5 µm, Mobile phase: $CO_2$/MeOH=60/40; Flow: 50 mL/min 230 nm ambient temperature. Analytical chiral HPLC: Chiralcel IC 250 mm×4.6 mm 5 µm, Mobile phase: Hexane/EtOH=70/30; Flow: 1.0 mL/min 230 nm ambient temperature; Retention time: 7.632 min. P1: 99.7% e.e. $[\alpha]^{254}_D = -64.6$ (c=0.01, MeOH). LC-MS for $C_{12}H_{10}FN_2O_2$+H⁺ [M+H]⁺: calcd. 215.1. found: 215.1. ¹H NMR (400 MHz, DMSO-$d_6$) δ [ppm]: 11.29 (s, 1H), 11.02 (s, 1H), 7.42 (d, J=8.0 Hz, 1H), 7.39 (d, J=8.1 Hz, 1H), 7.32 (d, J=2.4 Hz, 1H), 7.12-7.07 (m, 1H), 7.02-6.97 (m, 1H), 4.33 (dd, J=9.5, 5.3 Hz, 1H), 3.18 (dd, J=18.0, 9.5 Hz, 1H), 2.76 (dd, J=18.0, 5.3 Hz, 1H).

Compound 4a: (+)-(S)-3-(1H-indol-3-yl)pyrrolidine-2,5-dione

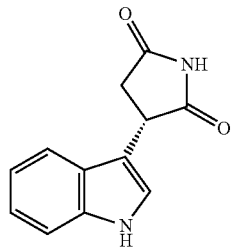

Isolated as second-eluting enantiomer from the chiral separation described for Compound 4a. Chiral HPLC retention time: 9.028 min. 99.6% e.e. $[\alpha]^{254}_D$=64.5 (c=0.01, MeOH).

Compound 5:
3-(5-chloro-1H-indol-3-yl)pyrrolidine-2,5-dione

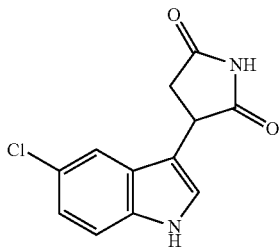 [SMILES: O=C1CC(c2c[nH]c3ccc(Cl)cc23)C(=O)N1]

Following the general method as outlined for compound 1, starting from 5-chloro-1H-indole (2.00 g; 13.2 mmol) and maleimide (3.84 g; 39.6 mmol), 160 mg (4.9%) of the title compound was obtained as a yellow solid after purification by silica gel chromatography (petroleum ether/EtOAc=3/1). LC-MS for $C_{12}H_9ClN_2O_2$—H⁻ calcd. 247.0. found: 247.0. ¹H NMR (300 MHz, DMSO-d₆) δ [ppm]: 11.30 (br s, 1H), 11.25 (br s, 1H), 7.49 (d, J=2.0 Hz, 1H), 7.42 (d, J=2.0 Hz, 1H), 7.39 (d, J=8.6 Hz, 1H), 7.10 (dd, J=8.6, 2.0 Hz, 1H), 4.36 (dd, J=9.5, 5.5 Hz, 1H), 3.17 (dd, J=18.0, 9.5 Hz, 1H), 2.80 (dd, J=18.0, 5.5 Hz, 1H).

Compound 6: (−)-(R)-3-(5-chloro-1H-indol-3-yl)pyrrolidine-2,5-dione

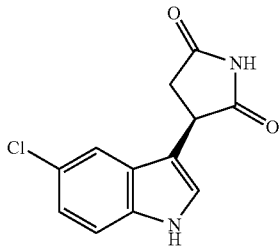 [SMILES: O=C1C[C@H](c2c[nH]c3ccc(Cl)cc23)C(=O)N1]

25 mg of the title compound was obtained by chiral preparative HPLC separation of 120 mg of compound 5. Preparative chiral HPLC: Chiralpak® IC 250 mm×20 mm 5 µm, Mobile phase: Hexane/EtOH=70/30; Flow: 15 mL/min 214 nm ambient temperature. Analytical chiral HPLC: Chiralpak® IC 250 mm×4.6 mm 5 µm, Mobile phase: Hexane/EtOH=70/30; Flow: 1.0 mL/min 230 nm ambient temperature; Retention time: 6.073 min. P1: 99.5% e.e. $[\alpha]^{254}_D$=−69.0 (c=0.0042, MeOH). LC-MS for $C_{12}H_9ClN_2O_2$+H⁺ [M+H]⁺: calcd. 249.0. found: 249.1. ¹H NMR (300 MHz, DMSO-d₆) δ [ppm]: 11.29 (br s, 1H), 11.25 (br s, 1H), 7.49 (d, J=2.0 Hz, 1H), 7.42 (d, J=2.4 Hz, 1H), 7.39 (d, J=8.6 Hz, 1H), 7.10 (dd, J=8.6, 2.0 Hz, 1H), 4.36 (dd, J=9.5, 5.5 Hz, 1H), 3.17 (dd, J=18.0, 9.5 Hz, 1H), 2.80 (dd, J=18.0, 5.5 Hz, 1H).

Compound 6a: (+)-(S)-3-(5-chloro-1H-indol-3-yl)pyrrolidine-2,5-dione

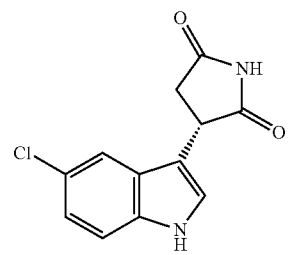

Isolated as second-eluting enantiomer from the chiral separation described for Compound 6a. Chiral HPLC retention time: 6.868 min. P1: 99.6% e.e. $[G]254_D$=67.4 (c=0.0038, MeOH).

Compound 7: 3-(6-chloro-5-fluoro-1H-indol-3-yl)pyrrolidine-2,5-dione

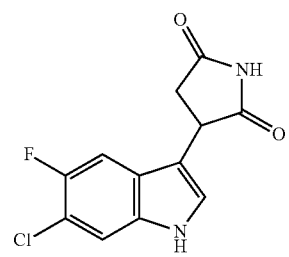 [SMILES: O=C1CC(c2c[nH]c3cc(Cl)c(F)cc23)C(=O)N1]

Following the general method as outlined for compound 1, starting from 6-chloro-5-fluoro-1H-indole (300 mg; 1.77 mmol) and maleimide (513 mg; 5.28 mmol), 110 mg (23%) of the title compound was obtained as a yellow solid after purification by preparative HPLC. LC-MS for $C_{12}H_6ClFN_2O_2$—H⁻ [M−H]⁻: calcd. 265.1. found: 265.0. ¹H NMR (300 MHz, DMSO-d₆) δ [ppm]: 11.30 (br s, 1H), 11.27 (br s, 1H), 7.54 (d, J=6.4 Hz, 1H), 7.47 (s, 1H), 7.46 (d, J=10.2 Hz, 1H), 4.35 (dd, J=9.4, 5.8 Hz, 1H), 3.16 (dd, J=18.0, 9.4 Hz, 1H), 2.81 (dd, J=18.0, 5.8 Hz, 1H).

Compound 8: (R)-3-(6-chloro-5-fluoro-1H-indol-3-yl)pyrrolidine-2,5-dione

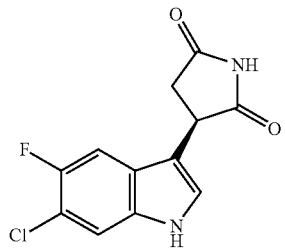 [SMILES: O=C1C[C@H](c2c[nH]c3cc(Cl)c(F)cc23)C(=O)N1]

25 mg of the title compound was obtained by chiral preparative HPLC separation of 70 mg of compound 7. Preparative chiral HPLC: Chiralpak® AS-H 250 mm×20 mm 5 µm, Mobile phase: $CO_2$/IPA=60/40; Flow: 50 mL/min 220 nm ambient temperature. Analytical chiral HPLC: Chiralpak® IA 250 mm×4.6 mm 5 µm, Mobile phase: $CO_2$/IPA/DEA=70/30/0.2; Flow: 1.0 mL/min 230 nm ambient temperature; Retention time: 3.72 min. P1: >99.5% e.e. LC-MS for $C_{12}H_6ClFN_2O_2$—H$^-$ [M–H]$^-$: calcd. 265.1. found: 265.1. $^1$H NMR (300 MHz, DMSO-$d_6$) δ [ppm]: 11.30 (br s, 1H), 11.27 (br s, 1H), 7.54 (d, J=6.4 Hz, 1H), 7.47 (s, 1H), 7.46 (d, J=10.2 Hz, 1H), 4.35 (dd, J=9.4, 5.8 Hz, 1H), 3.16 (dd, J=18.0, 9.4 Hz, 1H), 2.81 (dd, J=18.0, 5.8 Hz, 1H).

Compound 8a: (S)-3-(6-chloro-5-fluoro-1H-indol-3-yl)pyrrolidine-2,5-dione

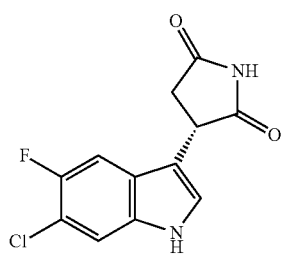

Isolated as second-eluting enantiomer from the chiral separation described for Compound 8a. Chiral HPLC retention time: 5.48 min. 99.6% e.e.

Compound 9: 3-(6-bromo-5-fluoro-1H-indol-3-yl)pyrrolidine-2,5-dione

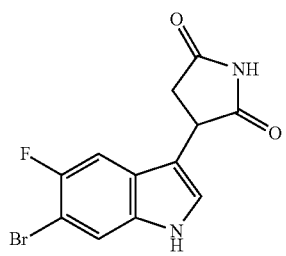

Following the general method as outlined for compound 1, starting from 6-bromo-5-fluoro-1H-indole (213 mg; 1.00 mmol) and maleimide (388 mg; 4.00 to mmol), 70 mg (23%) of the title compound was obtained as a yellow solid after purification by preparative HPLC. LC-MS for $C_{12}H_6BrFN_2O_2$—H$^-$ [M–H]$^-$: calcd. 309.0. found: 308.9. $^1$H NMR (300 MHz, DMSO-$d_6$) δ [ppm]: 11.31 (s, 1H), 11.27 (s, 1H), 7.66 (d, J=6.0 Hz, 1H), 7.48 (d, J=1.7 Hz, 1H), 7.44 (d, J=9.8 Hz, 1H), 4.36 (dd, J=9.2, 5.6 Hz, 1H), 3.17 (dd, J=18.0, 9.2 Hz, 1H), 2.82 (dd, J=18.0, 5.6 Hz, 1H).

Compound 10: (R)-3-(6-bromo-5-fluoro-1H-indol-3-yl)pyrrolidine-2,5-dione

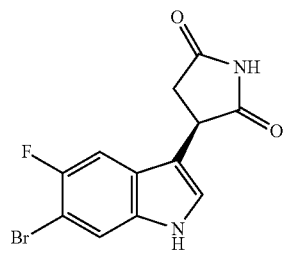

22 mg of the title compound was obtained by chiral preparative HPLC separation of 60 mg of compound 9. Preparative chiral HPLC: Chiralpak® AD-H 250 mm×20 mm 5 µm, Mobile phase: $CO_2$/MeOH=60/40; Flow: 50 mL/min 214 nm ambient temperature. Analytical chiral HPLC: Chiralpak® ID 250 mm×4.6 mm 5 µm, Mobile phase: $CO_2$/MeOH=60/40; Flow: 3.0 mL/min 230 nm ambient temperature; Retention time: 2.14 min. P1: >99.5% e.e. LC-MS for $C_{12}H_6BrFN_2O_2$—H$^-$ [M–H]$^-$: calcd. 309.0. found: 308.8. $^1$H NMR (300 MHz, DMSO-$d_6$) δ [ppm]: 11.31 (s, 1H), 11.27 (s, 1H), 7.66 (d, J=6.0 Hz, 1H), 7.48 (d, J=1.7 Hz, 1H), 7.44 (d, J=9.8 Hz, 1H), 4.36 (dd, J=9.2, 5.6 Hz, 1H), 3.17 (dd, J=18.0, 9.2 Hz, 1H), 2.82 (dd, J=18.0, 5.6 Hz, 1H).

Compound 10a: (S)-3-(6-bromo-5-fluoro-1H-indol-3-yl)pyrrolidine-2,5-dione

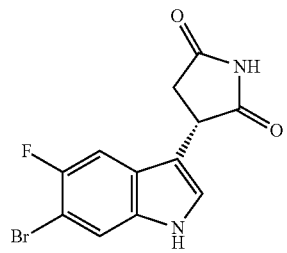

Isolated as second-eluting enantiomer from the chiral separation described for Compound 10a. Chiral HPLC retention time: 4.20 min. 98.9% e.e.

Compound 11:
3-(5-bromo-1H-indol-3-yl)pyrrolidine-2,5-dione

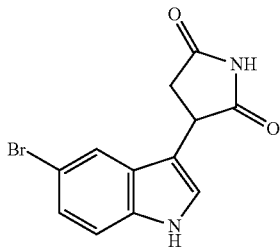

Following the general method as outlined for compound 1, starting from 5-bromo-1H-indole (500 mg; 2.56 mmol) and maleimide (666 mg; 6.86 mmol), 160 mg (21%) of the title compound was obtained as a yellow solid after purification by preparative HPLC. LC-MS for $C_{12}H_9BrN_2O_2+H^+$ [M+H]$^+$: calcd. 293.0. found: 293.0. $^1$H NMR (400 MHz, DMSO-d$_6$) δ [ppm]: 11.29 (s, 1H), 11.26 (s, 1H), 7.64 (d, J=1.8 Hz, 1H), 7.40 (d, J=2.4 Hz, 1H), 7.35 (d, J=8.6 Hz, 1H), 7.21 (dd, J=8.6, 1.8 Hz, 1H), 4.36 (dd, J=9.5, 5.5 Hz, 1H), 3.17 (dd, J=18.0, 9.5 Hz, 1H), 2.80 (dd, J=18.0, 5.5 Hz, 1H).

Compound 12:
3-(5-methyl-1H-indol-3-yl)pyrrolidine-2,5-dione

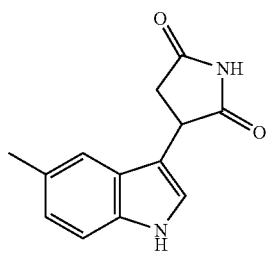 [SMILES: Cc1ccc2[nH]cc(C3CC(=O)NC3=O)c2c1]

Following the general method as outlined for compound 1, starting from 5-methyl-1H-indole (300 mg; 2.29 mmol) and maleimide (670 mg; 6.87 mmol), 200 mg (38%) of the title compound was obtained as a yellow solid after recrystallization in MeOH. LC-MS for $C_{13}H_{12}N_2O_2+H^+$ [M+H]$^+$: calcd. 229.1. found: 229.1. $^1$H NMR (400 MHz, DMSO-d$_6$) δ [ppm]: 11.27 (s, 1H), 10.88 (s, 1H), 7.26 (dd, J=8.3, 2.0 Hz), 7.25 (d, J=2.0 Hz, 1H), 7.19 (s, 1H), 6.92 (d, J=8.3 Hz, 1H), 4.29 (dd, J=9.5, 5.3 Hz, 1H), 3.16 (dd, J=18.0, 9.5 Hz, 1H), 2.74 (dd, J=18.0, 5.3 Hz, 1H), 2.36 (s, 3H).

Compound 13:
3-(5-methoxy-1H-indol-3-yl)pyrrolidine-2,5-dione

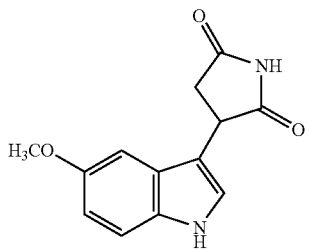 [SMILES: COc1ccc2[nH]cc(C3CC(=O)NC3=O)c2c1]

Following the general method as outlined for compound 1, starting from 5-methoxy-1H-indole (200 mg; 1.36 mmol) and maleimide (407 mg; 4.19 mmol), 170 mg (51%) of the title compound was obtained as a yellow solid after purification by preparative HPLC. LC-MS for $C_{13}H_{12}N_2O_3+H^+$ [M+H]$^+$: calcd. 245.1. found: 245.1. $^1$H NMR (400 MHz, DMSO-d$_6$) δ [ppm]: 11.25 (brs, 1H), 10.86 (s, 1H), 7.27 (d, J=2.2 Hz 1H), 7.26 (d, J=8.6 Hz, 1H), 6.91 (d, J=2.2 Hz, 1H), 6.76 (dd, J=8.6, 2.2 Hz, 1H), 4.30 (dd, J=9.6, 5.3 Hz, 1H), 3.74 (s, 3H), 3.18 (dd, J=17.9, 9.6 Hz, 1H), 2.75 (dd, J=17.9, 5.3 Hz, 1H).

Compound 14: 3-(2,5-dioxopyrrolidin-3-yl)-1H-indole-5-carbonitrile

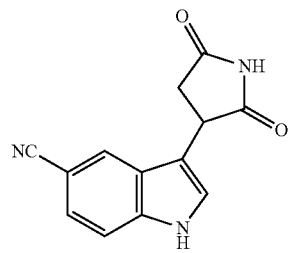

A mixture of 3-(5-bromo-1H-indol-3-yl)pyrrolidine-2,5-dione (compound 11; 500 mg; 1.71 mmol) and CuCN (231 mg; 2.58 mmol) in NMP (3 mL) was stirred at 200° C. for 1.5 h in a microwave reactor. The reaction mixture was purified by preparative HPLC to afford 110 mg (27%) of the title compound as a green solid. LC-MS for $C_{13}H_9N_3O_2+H^+$ [M+H]$^+$: calcd. 240.1. found: 240.1. $^1$H NMR (300 MHz, DMSO-d$_6$) δ [ppm]: 11.63 (brs, 1H), 8.04 (s, 1H), 7.57 (d, J=1.8 Hz, 1H), 7.54 (d, J=8.8 Hz, 1H), 7.45 (dd, J=8.6, 1.8 Hz, 1H), 4.44 (dd, J=9.5, 5.8 Hz, 1H), 3.18 (dd, J=17.8, 9.5 Hz, 1H), 2.87 (dd, J=17.8, 5.8 Hz, 1H).

Compound 15: 3-(5,6-difluoro-1H-indol-3-yl)pyrrolidine-2,5-dione

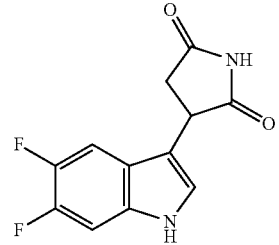 [SMILES: O=C1CC(c2c[nH]c3cc(F)c(F)cc23)C(=O)N1]

Following the general method as outlined for compound 1, starting from 5,6-difluoro-1H-indole (200 mg; 1.31 mmol) and maleimide (380 mg; 3.91 mmol), 15 mg (5%) of the title compound was obtained as a yellow solid after purification by preparative HPLC. LC-MS for $C_{12}H_8F_2N_2O_2+H^+$ [M+H]$^+$: calcd. 251.1. found: 251.0. $^1$H NMR (300 MHz, DMSO-d$_6$) δ [ppm]: 11.27 (brs, 1H), 11.21 (brs, 1H), 7.45 (dd, J=11.5, 8.0 Hz, 1H), 7.41 (d, J=1.8 Hz, 1H), 7.37 (dd, J=11.2, 7.0 Hz, 1H), 7.48-7.34 (m, 3H), 4.34 (dd, J=9.3, 5.6 Hz, 1H), 3.16 (dd, J=18.0, 9.3 Hz, 1H), 2.80 (dd, J=18.0, 5.6 Hz, 1H).

Compound 16: 3-(5-fluoro-6-methyl-1H-indol-3-yl)pyrrolidine-2,5-dione

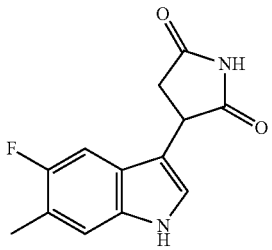 [SMILES: Cc1cc2[nH]cc(C3CC(=O)NC3=O)c2cc1F]

Following the general method as outlined for compound 1, starting from 5-fluoro-6-methyl-1H-indole (1.00 g; 6.70 mmol) and maleimide (2.10 g; 21.6 mmol), 4.2 mg (0.2%) of the title compound was obtained as a yellow solid after purification by preparative HPLC. LC-MS for $C_{13}H_{11}FN_2O_2+H^+$ $[M+H]^+$: calcd. 247.1. found: 247.1. $^1H$ NMR (300 MHz, DMSO-$d_6$) δ [ppm]: 11.28 (s, 1H), 10.99 (s, 1H), 7.31 (d, J=2.5 Hz, 1H), 7.22 (d, J=6.4 Hz, 1H), 7.13 (d, J=10.8 Hz, 1H), 4.29 (dd, J=9.4, 5.4 Hz, 1H), 3.16 (dd, J=18.0, 9.4 Hz, 1H), 2.76 (dd, J=18.0, 5.4 Hz, 1H), 2.30 (d J=1.6 Hz, 3H).

Compound 17: 3-(6-fluoro-1H-indol-3-yl)pyrrolidine-2,5-dione

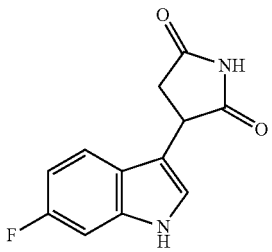 [SMILES: O=C1CC(c2c[nH]c3cc(F)ccc23)C(=O)N1]

Following the general method as outlined for compound 1, starting from 6-fluoro-1H-indole (4.00 g; 29.6 mmol) and maleimide (8.80 g; 90.7 mmol), 3.0 g (44%) of the title compound was obtained as an orange solid after purification by silica gel chromatography (petroleum ether/EtOAc=3/1-2/3). LC-MS for $C_{12}H_9FN_2O_2$—$H^-$ $[M-H]^-$: calcd. 231.1. found: 231.1. $^1H$ NMR (400 MHz, DMSO-$d_6$) δ [ppm]: 11.10 (s, 1H), 7.43 (dd, J=8.7, 5.4 Hz, 1H), 7.33 (d, J=2.0 Hz, 1H), 7.14 (dd, J=10.1, 2.3 Hz, 1H), 6.87 (td, J=9.8, 8.7, 2.3 Hz, 1H), 4.34 (dd, J=9.5, 5.4 Hz, 1H), 3.17 (dd, J=18.0, 9.5 Hz, 1H), 2.77 (dd, J=18.0, 5.4 Hz, 1H).

Compound 18: 3-(6-chloro-1H-indol-3-yl)pyrrolidine-2,5-dione

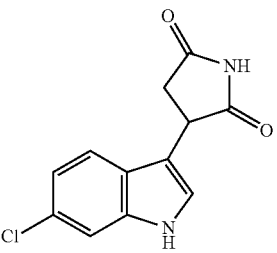 [SMILES: O=C1CC(c2c[nH]c3cc(Cl)ccc23)C(=O)N1]

Following the general method as outlined for compound 1, starting from 6-chloro-1H-indole (0.50 g; 3.3 mmol) and maleimide (0.96 g; 9.9 mmol), 100 mg (12%) of the title compound was obtained as a yellow solid after purification by silica gel chromatography (petroleum ether/EtOAc=5/1). LC-MS for $C_{12}H_9ClN_2O_2$—$H^-$ $[M-H]^-$: calcd. 247.0. found: 247.0. $^1H$ NMR (300 MHz, DMSO-$d_6$) δ [ppm]: 11.27 (brs, 1H), 11.17 (s, 1H), 7.45 (d, J=8.4 Hz, 1H), 7.41 (d, J=1.8 Hz, 1H), 7.38 (d, J=2.4 Hz, 1H), 7.03 (dd, J=8.4, 1.8 Hz, 1H), 4.34 (dd, J=9.5, 5.5 Hz, 1H), 3.17 (dd, J=18.0, 9.5 Hz, 1H), 2.77 (dd, J=18.0, 5.5 Hz, 1H).

Compound 19: 3-(6-bromo-1H-indol-3-yl)pyrrolidine-2,5-dione

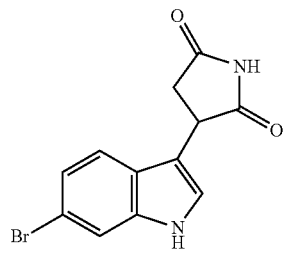

Following the general method as outlined for compound 1, starting from 6-bromo-1H-indole (2.00 g; 10.2 mmol) and maleimide (2.96 g; 30.5 mmol), 1.5 g (50%) of the title compound was obtained as a yellow solid after purification by preparative HPLC. LC-MS for $C_{12}H_9BrN_2O_2+H^+$ $[M+H]^+$: calcd. 293.0. found: 293.0. $^1H$ NMR (300 MHz, DMSO-$d_6$) δ [ppm]: 11.30 (brs, 1H), 11.18 (s, 1H), 7.56 (d, J=1.6 Hz, 1H), 7.41 (d, J=8.5 Hz, 1H), 7.37 (d, J=2.4 Hz, 1H), 7.14 (dd, J=8.5, 1.7 Hz, 1H), 4.34 (dd, J=9.5, 5.4 Hz, 1H), 3.17 (dd, J=18.0, 9.5 Hz, 1H), 2.77 (dd, J=18.0, 5.4 Hz, 1H).

Compound 20: 3-(6-methyl-1H-indol-3-yl)pyrrolidine-2,5-dione

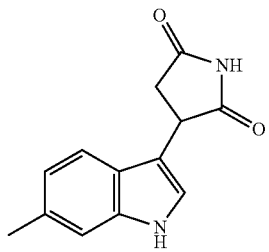 [SMILES: Cc1ccc2c(C3CC(=O)NC3=O)c[nH]c2c1]

Following the general method as outlined for compound 1, starting from 6-methyl-1H-indole (0.20 g; 1.52 mmol) and maleimide (0.44 g; 4.53 mmol), 0.22 g (63%) of the title compound was obtained as a yellow solid after purification by preparative HPLC. LC-MS for $C_{13}H_{12}N_2O_2$—$H^-$ $[M-H]^-$: calcd. 227.1. found: 227.1. $^1H$ NMR (300 MHz, DMSO-$d_6$) δ [ppm]: 10.85 (brs, 2H), 11.18 (s, 1H), 7.28 (d, J=8.0 Hz, 1H), 7.20 (d, J=2.3 Hz, 1H), 7.16 (s, 1H), 6.83 (d, J=8.0 Hz, 1H), 4.28 (dd, J=9.5, 5.3 Hz, 1H), 3.17 (dd, J=18.0, 9.5 Hz, 1H), 2.73 (dd, J=18.0, 5.3 Hz, 1H), 2.38 (s, 3H).

Compound 21:
3-(6-methoxy-1H-indol-3-yl)pyrrolidine-2,5-dione

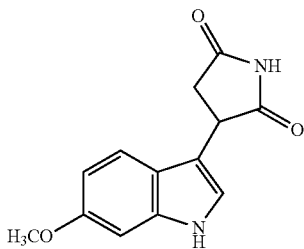

Following the general method as outlined for compound 1, starting from 6-methoxy-1H-indole (0.20 g; 1.36 mmol) and maleimide (0.40 g; 4.12 mmol), 80 mg (24%) of the title compound was obtained as a yellow solid after purification by preparative HPLC. LC-MS for $C_{13}H_{12}N_2O_3$—H⁻ [M−H]⁻: calcd. 243.1. found: 243.1. ¹H NMR (400 MHz, DMSO-d₆) δ [ppm]: 11.26 (s, 1H), 10.81 (s, 1H), 7.29 (d, J=8.7 Hz, 1H), 7.16 (d, J=2.2 Hz, 1H), 6.86 (d, J=2.2 Hz, 1H), 6.66 (dd, J=8.7, 2.2 Hz, 1H), 4.27 (dd, J=9.5, 5.2 Hz, 1H), 3.75 (s, 3H), 3.16 (dd, J=18.0, 9.5 Hz, 1H), 2.73 (dd, J=18.0, 5.2 Hz, 1H).

Compound 22: 3-(2,5-dioxopyrrolidin-3-yl)-1H-indole-6-carbonitrile

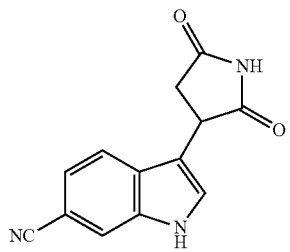 [SMILES: N#Cc1ccc2c(C3CC(=O)NC3=O)c[nH]c2c1]

Following the general method as outlined for compound 14, starting from 3-(6-bromo-1H-indol-3-yl)pyrrolidine-2,5-dione (compound 19; 0.20 g; 0.68 mmol) and CuCN (90 mg; 1.00 mmol), 14 mg (8.6%) of the title compound was obtained as a yellow solid after purification by preparative HPLC. LC-MS for $C_{13}H_9N_3O_2$+H⁺[M+H]⁺: calcd. 240.1. found: 240.1. ¹H NMR (300 MHz, DMSO-d₆) δ [ppm]: 11.63 (brs, 1H), 11.32 (s, 1H), 7.88 (s, 1H), 7.68-7.62 (m, 2H), 7.35 (dd, J=9.5, 5.6 Hz, 1H), 4.42 (dd, J=17.8, 9.5 Hz, 1H), 3.18 (dd, J=18.0, 9.9 Hz, 1H), 2.82 (dd, J=17.8, 5.6 Hz, 1H).

Compound 23:
3-(naphthalen-1-yl)pyrrolidine-2,5-dione

To a solution of naphthalen-1-ylboronic acid (0.27 g; 1.57 mmol) in 1,4-dioxane (9 mL) and water (1.4 mL) was added Et₃N (0.10 g; 0.99 mmol), [RhOH(cod)]₂ (23 mg; 0.05 mmol) and maleimide (100 mg; 1.03 mmol). The dark brown mixture was heated at 50° C. for 2.5 h, cooled to room temperature, and concentrated in vacuo. The residue was diluted with H₂O (10 mL) and extracted with DCM (20 mL×3). The combined organic layers were dried over anhydrous Na₂SO₄, filtered, concentrated, and purified by preparative HPLC to afford 136 mg (59%) of the title compound as a white solid. LC-MS for $C_{14}H_{11}NO_2$—H⁻ [M−H]⁻: calcd. 224.1. found: 224.1. ¹H NMR (300 MHz, DMSO-d₆) δ [ppm]: 11.50 (s, 1H), 8.02-7.95 (m, 2H), 7.89 (d, J=9.1 Hz, 1H), 7.63-7.53 (m, 2H), 7.53-7.46 (m, 1H), 7.41 (d, J=7.1 Hz, 1H), 4.96 (dd, J=9.6, 5.7 Hz, 1H), 3.32 (dd, J=18.0, 9.6 Hz, 1H), 2.71 (dd, J=18.0, 5.7 Hz, 1H).

Compound 24:
3-(6-fluoronaphthalen-1-yl)pyrrolidine-2,5-dione

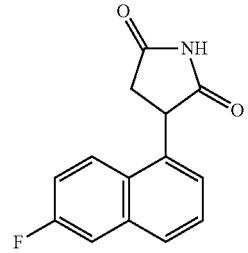

Step 1: 6-fluoronaphthalene-1-diazonium tetrafluoroborate

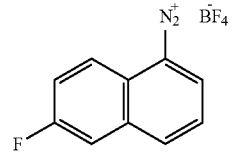

To a solution of 6-fluoronaphthalen-1-amine (500 mg; 3.10 mmol) and HBF₄ (40%; 2 mL, 12.6 mmol) in H₂O (2 mL) at 0° C. was added a cold solution of NaNO₂ (214 mg; 3.10 mmol) in H₂O (0.5 mL) dropwise. The reaction was stirred at room temperature for 1 h. The precipitate was collected by filtration, washed with EtOH (5 mL), Et₂O (5 mL), and dried under vacuum to afford 0.40 g (50%) of the title compound as a pale solid, which was used to directly in the next step without further purification.

Step 2: 2-(6-fluoronaphthalen-1-yl)succinic acid

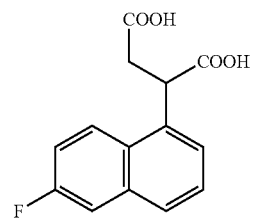

Maleic anhydride (150 mg; 1.54 mmol) was added with to an aqueous NaOH solution (4 M, 0.70 mL, 2.8 mmol). The resulting solution was added at 0-5° C. to an aqueous TiCl₃ solution (15%, 3.2 g; 3.11 mmol), followed by acetone (2 mL). The cooling bath was removed and 6-fluoronaphthalene-1-diazonium tetrafluoroborate (Step 1: 400 mg; 1.54 mmol) was added slowly over 0.7 h. The suspension was stirred at room temperature for 1.5 h, concentrated to remove acetone, and extracted with Et₂O (10 mL×3). The aqueous layer was acidified to pH-1 with HCl (1 M) and extracted with EtOAc (10 mL×3). The combined organic layers were dried over anhydrous Na₂SO₄, filtered, and concentrated to afford 190 mg (47%) of the title compound as a brown solid, which was used directly in the next step without further purification. LC-MS for $C_{14}H_{11}FO_4+NH_4^+$ $[M+NH_4]^+$: calcd. 280.1. found: 280.0.

Step 3

A mixture of 2-(6-fluoronaphthalen-1-yl)succinic acid (190 mg; 0.72 mmol) and urea (170 mg; 2.83 mmol) was stirred at 180° C. for 1 h. The reaction mixture was purified by silica gel chromatography (petroleum ether/EtOAc=1/1) to give a yellow solid, which was further purified by preparative HPLC to afford 63 mg (36%) the title compound as a white solid. LC-MS for $C_{14}H_{10}FNO_2+H^+$ $[M+H]^+$: calcd. 244.1. found: 243.9. ¹H NMR (300 MHz, DMSO-d₆) δ [ppm]: 8.08 (dd, J=9.3, 5.6 Hz, 1H), 7.87 (d, J=8.2 Hz, 1H), 7.76 (dd, J=10.2, 2.7 Hz, 1H), 7.56-7.46 (m, 2H), 7.38 (d, J=6.6 Hz, 1H), 4.95 (dd, J=9.4, 5.6 Hz, 1H), 3.30 (dd, J=18.0, 9.4 Hz, 1H), 2.71 (dd, J=18.0, 5.6 Hz, 1H).

Compound 25:
3-(7-fluoronaphthalen-1-yl)pyrrolidine-2,5-dione

Step 1: 7-fluoronaphthalene-1-diazonium tetrafluoroborate

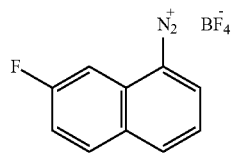

Following the general method as outlined for compound 24—Step 1, starting from 7-fluoronaphthalen-1-amine (300 mg; 1.86 mmol), HBF₄ (40%; 1.5 mL, 9.4 mmol), H₂O (5 mL), NaNO₂ (260 mg; 3.77 mmol) in H₂O (4 mL), 300 mg (62%) of the title compound was obtained as a pale solid, which was used to directly in the next step without further purification. LC-MS for $C_{10}H_6FN_2^+$ $[M]^+$: calcd. 173.1. found: 173.0.

Step 2: 2-(7-fluoronaphthalen-1-yl)succinic acid

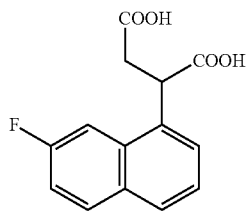 [SMILES: O=C(O)CC(C(=O)O)c1cccc2ccc(F)cc12]

Following the general method as outlined for compound 24—Step 2, starting from maleic anhydride (110 mg; 1.12 mmol), aqueous NaOH solution (4 NA; 0.7 mL, 2.8 mmol), aqueous TiCl₃ solution (15%, 2.36 g; 2.32 mmol), acetone (2 mL), and 7-fluoronaphthalene-1-diazonium tetrafluoroborate (Step 1: 300 mg; 1.15 mmol), 200 mg (66%) of the title compound was obtained as a brown solid, which was used directly in the next step without further purification.

Step 3

Following the general method as outlined for compound 24—Step 3, starting from 2-(7-fluoronaphthalen-1-yl)succinic acid (Step 2; 200 mg; 0.76 mmol) and urea (180 mg; 3.00 mmol), 3.3 mg (1.8%) of the title compound was obtained as a white solid after purification by silica gel chromatography (petroleum ether/EtOAc=1/1) and preparative HPLC. LC-MS for $C_{14}H_{10}FNO_2-H^-$ $[M-H]^-$: calcd. 242.1. found: 242.0. ¹H NMR (300 MHz, MeOH-d₄) δ [ppm]: 7.99 (dd, J=9.0, 5.9 Hz, 1H), 7.88 (dd, J=6.8, 2.0 Hz, 1H), 7.70 (d, J=11.1, 2.0 Hz, 2H), 7.50-7.42 (m, 1H), 7.41-7.32 (m, 1H), 4.88 (dd, J=9.5, 5.1 Hz, 1H), 3.43 (dd, J=18.2, 9.5 Hz, 1H), 2.72 (dd, J=18.2, 5.1 Hz, 1H).

Compound 26:
3-(6-chloronaphthalen-1-yl)pyrrolidine-2,5-dione

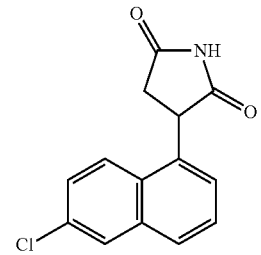

Step 1: 6-chloronaphthalene-1-diazonium tetrafluoroborate

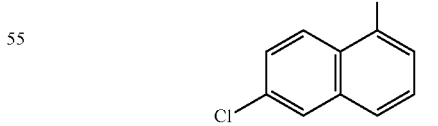

Following the general method as outlined for compound 24—Step 1, starting from 6-chloronaphthalen-1-amine (1.00 g; 5.63 mmol), HBF₄ (40%; 4 mL, 25.2 mmol), H₂O (4 mL), and NaNO₂ (390 mg; 5.65 mmol) in H₂O (1 mL), 1.50 g (96%) of the title compound as a purple solid, which was used to directly in the next step without further purification. LC-MS for $C_{10}H_6ClN_2^+$ $[M]^+$: calcd. 189.0. found: 188.9.

Step 2: 2-(6-chloronaphthalen-1-yl)succinic acid

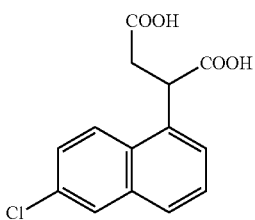 [SMILES: O=C(O)CC(C(=O)O)c1cccc2cc(Cl)ccc12]

Following the general method as outlined for compound 24—Step 2, starting from maleic anhydride (216 mg; 2.20 mmol), aqueous NaOH solution (4 NA; 6.0 mL, 24 mmol), aqueous TiCl$_3$ solution (15%, 4.5 g; 4.4 mmol), acetone (2 mL), and 6-chloronaphthalene-1-diazonium tetrafluoroborate (Step 1: 600 mg; 2.17 mmol), 600 mg (99%) of the title compound was obtained as a black solid, which was used directly in the next step without further purification.

Step 3

Following the general method as outlined for compound 24—Step 3, starting from 2-(6-chloronaphthalen-1-yl)succinic acid (Step 2; 600 mg; 2.15 mmol) and urea (600 mg; 9.99 mmol), 10 mg (2%) of the title compound was obtained as a yellow solid after purification by silica gel chromatography (petroleum ether/EtOAc=2/1) and preparative HPLC. LC-MS for $C_{14}H_{10}ClNO_2-H^-$ [M−H]$^-$: calcd. 258.0. found: 257.9. $^1$H NMR (400 MHz, MeOH-d$_4$) δ [ppm]: 8.02 (d, J=9.0 Hz, 1H), 7.96 (d, J=1.8 Hz, 1H), 7.81 (d, J=8.3 Hz, 1H), 7.57-7.49 (m, 2H), 7.42 (d, J=7.3 Hz, 1H), 4.96 (dd, J=9.8, 5.3 Hz, 1H), 3.44 (dd, J=18.3, 9.8 Hz, 1H), 2.77 (dd, J=18.2, 5.3 Hz, 1H).

Compound 27:
3-(7-chloronaphthalen-1-yl)pyrrolidine-2,5-dione

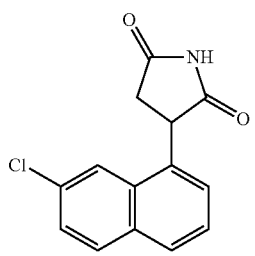 [SMILES: O=C1CC(c2cccc3ccc(Cl)cc23)C(=O)N1]

Step 1: 7-chloronaphthalene-1-diazonium tetrafluoroborate

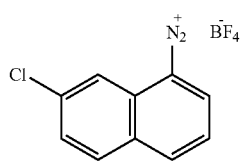

Following the general method as outlined for compound 24—Step 1, starting from 7-chloronaphthalen-1-amine (0.45 g; 2.53 mmol), HBF$_4$ (40%; 2.5 mL, 15.7 mmol), H$_2$O (2 mL), and NaNO$_2$ (190 mg; 2.75 mmol) in H$_2$O (4 mL), 400 mg (57%) of the title compound as a pale solid, which was used to directly in the next step without further purification. LC-MS for $C_{10}H_6ClN_2^+$ [M]$^+$: calcd. 189.0. found: 188.9.

Step 2: 2-(7-chloronaphthalen-1-yl)succinic acid

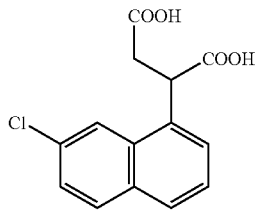 [SMILES: O=C(O)CC(C(=O)O)c1cccc2ccc(Cl)cc12]

Following the general method as outlined for compound 24—Step 2, starting from maleic anhydride (213 mg; 2.17 mmol), aqueous NaOH solution (4 NA; 0.7 mL, 2.8 mmol), aqueous TiCl$_3$ solution (15%, 4.46 g; 4.3 mmol), acetone (2 mL), and 7-chloronaphthalene-1-diazonium tetrafluoroborate (Step 1: 600 mg; 2.17 mmol), 500 mg (83%) of the title compound was obtained as a brown solid, which was used directly in the next step without further purification.

Step 3

Following the general method as outlined for compound 24—Step 3, starting from 2-(7-chloronaphthalen-1-yl)succinic acid (Step 2; 500 mg; 1.79 mmol) and urea (430 mg; 7.16 mmol), 2.5 mg (0.5%) of the title compound was obtained as a white solid after purification by silica gel chromatography (petroleum ether/EtOAc=1/1) and preparative HPLC. LC-MS for $C_{14}H_{10}ClNO_2+H^+$ [M+H]$^+$: calcd. 260.0. found: 260.0. $^1$H NMR (300 MHz, MeOH-d$_4$) δ [ppm]: 8.08 (s, 1H), 7.95 (d, J=8.7 Hz, 1H), 7.88 (d, J=8.4 Hz, 1H), 7.59-7.53 (m, 3H), 4.94 (dd, J=9.6, 5.4 Hz, 1H), 3.44 (dd, J=18.3, 9.6 Hz, 1H), 2.75 (dd, J=18.3, 5.4 Hz, 1H).

II. Biology Examples

II.1. Assay for IDO1 Enzymatic Activity Determination

The compounds of the present invention inhibit the enzymatic activity of human IDO1.

To measure enzymatic activity of human IDO1, the reaction mixture contained (final concentrations) potassium phosphate buffer (50 mM, pH 6.5), ascorbic acid (10 mM), methylene blue (5 μM) and human recombinant IDO1 enzyme (prepared as described in Rohrig et al. J Med Chem, 2012, 55, 5270-5290; final concentration 5 μg/mL) without or with the compounds of the present invention at the indicated concentrations (total volume 112.5 μL). The reaction was initiated by the addition of 37.5 μL of L-Trp (final concentration 100 μM) at room temperature. The reaction was conducted at room temperature during 15 minutes and stopped by the addition of 30 μL of 30% (w/v) trichloroacetic acid.

To convert N-formylkynurenine into kynurenine, the reaction mixture was incubated at 65° C. for 30 min. Then 120 μL of 2.5% (w/v) 4-(dimethylamino)-benzaldehyde in acetic acid were added and the mixture incubated for 5 min at room temperature. Kynurenine concentrations were determined by measuring the absorbance at 480 nm. A standard curve was made with pure kynurenine. The IDO1 activity was measured as described above using ten serial concentrations of the compounds of the present invention. Data were fitted using the Prism software (GraphPad Software, Inc.).

The biological activity of representative compounds is summarized in the following table:

| Compound | IC$_{50}$ (µM) |
|---|---|
| 1 | 0.15 |
| 1a | 0.21 |
| 2 | 0.12 |
| 2a | >50 |
| 3 | 3.0 |
| 4 | 1.8 |
| 4a | >50 |
| 5 | 2.1 |
| 6 | 2.2 |
| 6a | >50 |
| 7 | 0.49 |
| 9 | 0.29 |
| 10 | 0.62 |
| 10a | 8.0 |
| 11 | 0.37 |
| 12 | 53 |
| 13 | 53 |
| 14 | 12 |
| 15 | 1.8 |
| 16 | 46 |
| 17 | 3.4 |
| 18 | 2.1 |
| 19 | 0.42 |
| 20 | 54 |
| 22 | 1.7 |
| 23 | 18 |
| 24 | 1.7 |
| 25 | 4.6 |

In one embodiment, compounds with an IC50 below 5 µM are generally desirable to be selected for further study.

II.2. A Cellular Assay for IDO Activity Determination: hIDO1 P815 Cells

The compounds of the present invention inhibit the activity of human IDO in hIDO1 P815 cells [(ATCC® TIB-64™), *Mus musculus* mastocytoma cell)], available from American Type Culture Collection (ATCC), Manassas Va.].

The assay was performed in 96-well flat bottom plates seeded with P815 cells overexpressing hIDO1 (prepared as described in Rohrig et al. J Med Chem, 2012, 55, 5270-5290), at a concentration of 2×10$^5$ cells/well in a final volume of 200 µL. To determine IDO1 activity, the cells were incubated 24 hours at 37° C. at 5% CO$_2$ in IMDM (Invitrogen) supplemented with 2% FBS and 2% penicillin/streptomycin in the presence of the compounds of the present invention, at different concentrations.

The plates were then centrifuged 5 min at 1000 rpm, and 100 µL of the supernatant were collected in a conical plate, 30 µL of TCA 30% were added and a further centrifugated at 3000×g for 10 minutes. 100 µL of the supernatant were collected in a flat bottomed plate and 100 µL of 2% (w/v) 4-(dimethylamino)-benzaldehyde in acetic acid and incubated for 5 min at room temperature. Kynurenine concentrations were determined by measuring the absorbance at 480 nm. A standard curve was made with pure kynurenine. The IDO1 activity was measured as described above using ten different concentrations of the compounds of the present invention. Data were fitted using the Prism software (GraphPad Software, Inc.).

The biological activity of representative compounds is summarized in the following table:

| Compound | IC$_{50}$ (µM) |
|---|---|
| 1 | 0.094 |
| 2 | 0.009 |
| 2a | 0.45 |
| 3 | 0.92 |
| 4 | 0.24 |
| 4a | 3.30 |
| 5 | 0.59 |
| 15 | 0.26 |
| 18 | 0.50 |

In one embodiment, compounds with an IC50 below 5 µM are generally desirable to be selected for further study.

II.2.B Cellular Assay for IDO1 Activity Determination: HeLa Cells

The compounds of the present invention inhibit the activity of human IDO1 in HeLa cells [human adenocarcinoma Cells,® CCL-2™].

The assay was performed in 96-well flat bottom plates seeded with the human cervical cancer HeLa cell line with stimulation with IFNL.

To adhere HeLa cells (concentration of 5×10$^3$ cells/well) were incubated overnight at 37° C. at 5% CO$_2$ in EMEM (Lonza) supplemented with 10% FBS, 2% penicillin/streptomycin and 2 mM Ultraglutamin, in a final volume of 200 µL.

To stimulate the expression of IDO1, cells were then incubated two days at 37° C. at 5% CO$_2$ in EMEM (Lonza) supplemented with 2% FBS, 2% penicillin/streptomycin and 2 mM Ultraglutamine and 100 ng/mL IFNγ (R&D).

To determine IDO1 activity, medium was removed then the cells were incubated one day at 37° C. at 5% CO$_2$ in EMEM (Lonza) supplemented with 2% FBS and 2% penicillin/streptomycin in the presence of the compounds of the present invention, at different concentrations. Then 100 µL of the supernatant were collected in a conical plate, 30 uL of TCA 30% were added and a centrifugation was made at 3000×g for 10 minutes. 100 µL of the supernatant were collected in a flat bottom plate and 100 µL of 2% (w/v) 4-(dimethylamino)-benzaldehyde in acetic acid and incubated for 5 min at room temperature. Kynurenine concentrations were determined by measuring the absorbance at 480 nm. A standard curve was made with pure kynurenine. Data were fitted using the Prism software (GraphPad Software, Inc.).

The biological activity of representative compounds is summarized in the following table:

| Compound | IC$_{50}$ (µM) |
|---|---|
| 1 | 1.0 |
| 2 | 0.77 |
| 6 | 3.4 |
| 8 | 3.6 |
| 9 | 7.0 |
| 11 | 5.9 |

In one embodiment, compounds with an IC50 below 5 μM are generally desirable to be selected for further study.

II.2.0 Assay for IDO1 Activity Determination in Human Blood: Whole Blood Leukocyte Concentrate The compounds of the present invention inhibit the activity of human IDO1 in a human whole blood assay (whole blood leukocyte concentrate).

The human whole blood leukocyte concentrate was obtained as a byproduct in the manufacturing of red blood cell and platelet concentrate from a whole blood donation (as described in van der Meer et al., Vox Sang, 1999, 76(2), 90-99).

The assay was performed in 96-well flat bottom plates containing undiluted human whole blood leukocyte concentrate (with 2% penicillin/streptomycin) stimulated with lipopolysaccharide (LPS) (12.5 μg/mL) and recombinant human gamma interferon (rhIFNg) (50 ng/mL) for 18 hours to induce conversion of tryptophan to kynurenine. Plasma was collected after centrifugation and plasma kynurenine levels were determined LC-MS/MS (HPLC column Unison™ UK-Phenyl, 75×4.6, 3 μm, flow rate 0.8 mL/min, 4 minutes gradient from water+0.2% acetic acid to methanol+0.1% formic acid, retention time 2.7 min; API 4000™ MS-MS system from AB Sciex, ESI+ mode, parent ion 209.2, daughter ion 94.1).

To determine the effect of IDO1 inhibition on kynurenine production, the compounds of the present invention were co-incubated at different concentrations. Data were fitted using the Prism software (GraphPad Software, Inc.).

The biological activity of representative compounds is summarized in the following table (results are the average of the results with blood from several different donors):

| Compound | IC$_{50}$ (μM) ± Standard Deviation | Number of individual blood donors |
|---|---|---|
| 1 | 3.36 ± 0.51 | 13 |
| 2 | 3.26 ± 0.71 | 15 |

II.2.D Cellular Assay for IDO1-Dependent T Cell Proliferation Determination: SKOV-3 PBMC Co-Culture The compounds of the present invention restore T-cell proliferation in a SKOV-3 PBMC co-culture assay.

The assay was performed in 96-well flat bottom plates seeded with the human ovarian adenocarcinoma SKOV-3 cell line [SKOV-3; SKOV3] (ATCC® HTB-77™)] and co-cultured with human peripheral blood mononuclear cells (PBMC) stimulated with CD3/CD28 beads and rhIL-2.

To adhere, irradiated SKOV-3 cells (concentration of 150×10$^3$ cells/well) were incubated overnight at 37° C. at 5% CO$_2$ in Iscove's Modified Dulbecco's Medium (IMDM) (Lonza) supplemented with 50% FBS, 2% penicillin/streptomycin and 2 mM Ultraglutamin, in a final volume of 150 μL. Isolated PBMCs (stimulated with CD3/CD28 beads and rhIL-2 (30 U/mL)) were added in a ratio of 1:1. After 24 h of co-culture $^3$H-Thymidine (1 μCurie/10 uL) was added to assess proliferation (TopCount counter, Perkin Elmer) after overnight incubation in the presence of 50% serum.

To determine the effect of IDO1 inhibition on restoration of T cell proliferation, the compounds of the present invention were co-incubated at different concentrations.

Compound 2 showed an EC$_{50}$ of 0.074 μM in this assay (average of three independent experiments). FIG. 1 shows the effect of increasing concentrations of Compound 2 on Thymidine incorporation.

II.3. In-Vivo Inhibition of Blood Kynurenine Levels in Healthy Mice

The compounds of the present invention reduce the amount of Kynurenine in healthy mouse blood.

Briefly, mice were treated with either a suspension of one of the compounds of the present invention in 0.5% hydroxypropyl methylcellulose (HPMC) K4M/0.25% Tween 20 at different doses, or with a vehicle control (0.5% HPMC K4M/0.25% Tween 20), by the oral route by gavage (dosing volume 5 mL/kg, 10 mice per group). After two hours, blood was harvested, plasma was prepared and the amount of Kynurenine present was determined by LC-MS-MS (HPLC column Unison UK-Phenyl, 75×4.6, 3 μm, flow rate 0.8 mL/min, 4 minutes gradient from water+0.2% acetic acid to methanol+0.1% formic acid, retention time 2.7 min; AP14000™ MS-MS system from AB Sciex, ESI+ mode, parent ion 209.2, to daughter ion 94.1).

Compound 1 inhibited circulating Kynurenine by 41% at 100 mg/kg (p<0.0001) and by 59% at 200 mg/kg (p<0.0001): see table below.

| | Vehicle | Cpd. 1 100 mg/kg | Cpd. 1 200 mg/kg |
|---|---|---|---|
| Kynurenine concentration in plasma (average ± standard error of the mean) | 187.6 ± 17.8 ng/mL | 111.1 ± 27.0 ng/mL | 77.7 ± 9.2 ng/mL |

Figure 2:
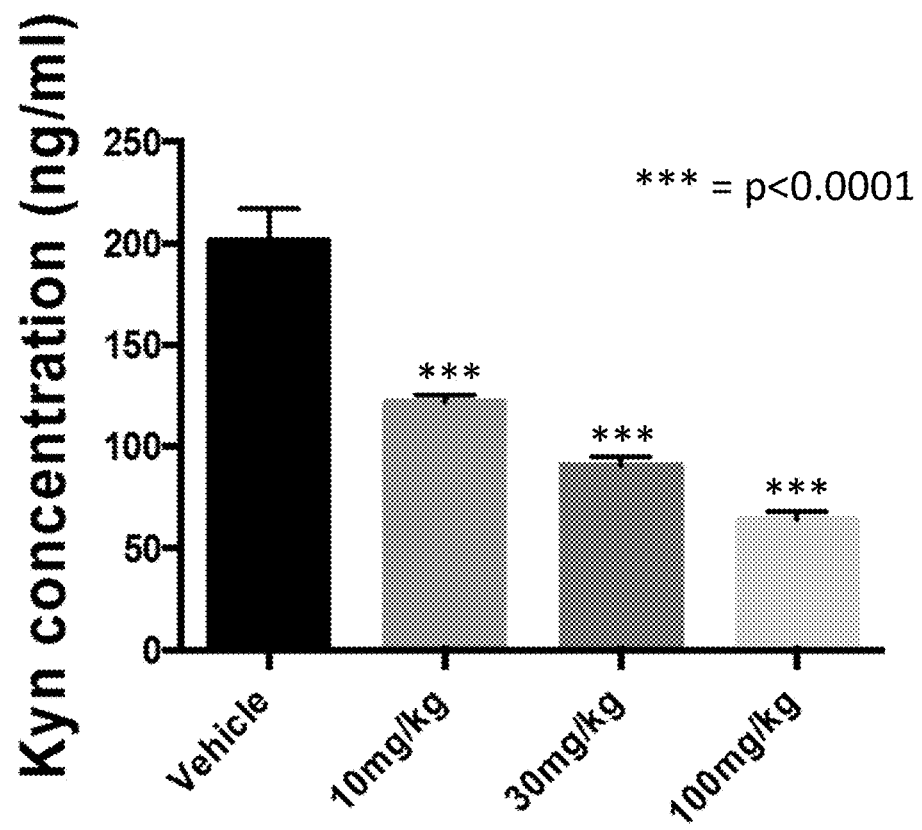
FIG. 2 is a graph showing the circulating Kynurenine concentration in healthy mouse blood after treatment with compound 2 of the invention or with a vehicle.

Compound 2 inhibited circulating Kynurenine by 39% at 10 mg/kg (p<0.0001), by 55% at 30 mg/kg (p<0.0001) and by 68% at 100 mg/kg (p<0.0001): see table below and FIG. 2.

| | Vehicle | Cpd. 2 10 mg/kg | Cpd. 2 30 mg/kg | Cpd. 2 100 mg/kg |
|---|---|---|---|---|
| Kynurenine concentration in plasma (average ± standard error of the mean) | 201 ± 15.7 ng/mL | 122 ± 3.5 ng/mL | 91.0 ± 4.4 ng/mL | 64.0 ± 3.8 ng/mL |

Example II.4: In Vivo Efficacy Studies in 4T1 Breast Cancer Syngeneic Model

In vivo efficacy studies for Compounds of the present invention were performed on 4T1 syngeneic tumor model of Balb/c mice implanted orthotopically in the mammary gland. One hundred thousand 4T1 breast cancer cells (ATCC® CRL-2539™)] were implanted orthotopically within the mammary gland of 7 weeks old Balb/c mice (day 0). Animals were randomized based on tumor size when tumor average reached 60 mm$^3$ (between day 7 and 11) into different treatment cohorts. The Compound of the present invention was administered orally twice per day (approximately at 9 am and 5 μm) starting the day of randomization. The Compounds were suspended into Methocel™ cellulose ether vehicle and sonicated before oral administration to animals using gavage needles. Treatment was administered daily until the end of the study. All experimental animals were monitored for body weight changes twice weekly. Tumor volume was measured twice a week by a caliper device and calculated with the following formula: Tumor volume=0.5×(length×width$^2$). Studies were terminated before tumor volumes reached 2000 mm. TGI (% tumor growth inhibition) was determined as $$\left(1-\left(\frac{Tx-T0}{Cx-C0}\right)\right)*100.$$

Figure 3:
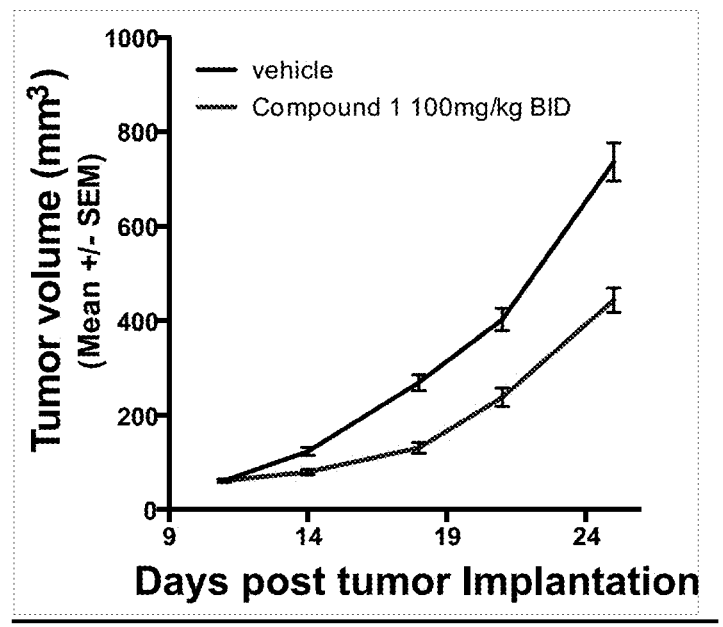
FIG. 3 is a graph of different studies showing the tumor growth of 4T1 tumors in a mouse breast cancer model after treatment with compound 1 or with a vehicle.

The table below and FIG. 3A show that Compound 1 inhibits 4T1 tumor growth in vivo.

| Treatment | Mean tumor volume (mm$^3$) on day 25 | TGI (Tumor growth inhibition) |
|---|---|---|
| Vehicle Methocel | 736.4 | 0% |
| Compound 1 100 mg/kg BID | 443.7 | 43.4% |

Example II.5: In Vivo Efficacy Studies with PancO2 Pancreatic Cancer Syngeneic Model In vivo efficacy studies of the Compounds of the present invention were performed on PancO2 syngeneic tumor model of C57/Bl6 mice implanted subcutaneously. Five millions PancO2 pancreas cancer cells were implanted subcutaneously to 7 weeks old C57/Bl6 mice (clay 0). Animals were randomized based on tumor size when tumor average reached 60 mm$^3$ (between day 10 and 12) into different treatment cohorts. The Compound was administered orally twice per day (approximately at 9 am and 5 pm) starting the day of randomization. The Compound was suspended into Methocel vehicle and sonicated before oral administration to animals using gavage needles. Treatment was administered daily until the end of the study. All experimental animals were monitored for body weight changes weekly. Tumor volume was measured weekly using a caliper device and calculated with the following formula: Tumor volume=0.5×(lengh×width$^2$). Studies were terminated before tumor volumes reached 2000 mm. TGI (% tumor growth inhibition) was determine as $$\left(1-\left(\frac{Tx-T0}{Cx-C0}\right)\right)*100.$$

Figure 4:
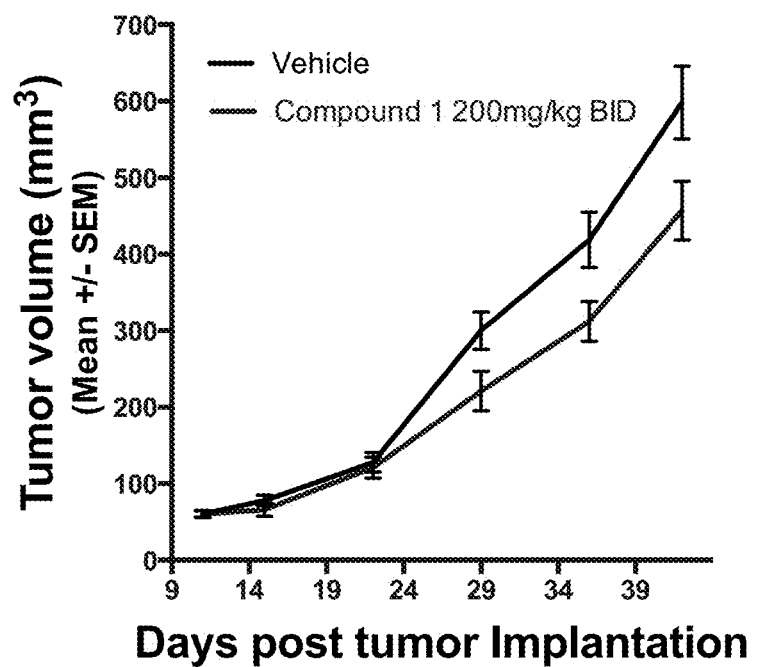
FIG. 4 is a graph showing the tumor growth of PanCO2 tumors in mice after treatment with test compounds. The upper line represents vehicle and the lower line represents compound 1.

The table below and FIG. 4 show that Compound 1 inhibits PancO2 tumor growth in vivo.

| Treatment | Mean tumor volume (mm$^3$) on day 42 | TGI (Tumor growth inhibition) |
|---|---|---|
| Vehicle Methocel | 598.2 | 0% |
| Compound 1 200 mg/kg BID | 457.0 | 26.2% |

In a separate study performed under the same conditions, Compound 2 (100 mg/kg BID) was studied. Methocel vehicle or 100 mg/kg of Compound 2 was administered orally twice per day (8 hours apart) starting the day of randomization. Compound 2 was resuspended into Methocel vehicle and sonicated before oral administration to animals using gavage needles. Treatment was administered daily until the end of the study. Tumor volume was measured weekly using a caliper device and calculated with the following formula: Tumor volume=0.5×(length×width$^2$). Mice were considered as dead when tumor size reached 400 mm$^3$. The table below show that Compound 2 inhibits PancO2 tumor growth in vivo. SEM refers to standard error of measurement.

| Treatment | Mean tumor volume (mm$^3$) +/− SEM on day 55 | TGI +/− SEM (Tumor growth inhibition) |
|---|---|---|
| Vehicle Methocel ® | 677.6 +/− 39.2 | 0% |
| Compound 2 - 100 mg/kg BID | 586.6 +/− 48.4 | 16.8% +/− 8.2 |

Figure 5:
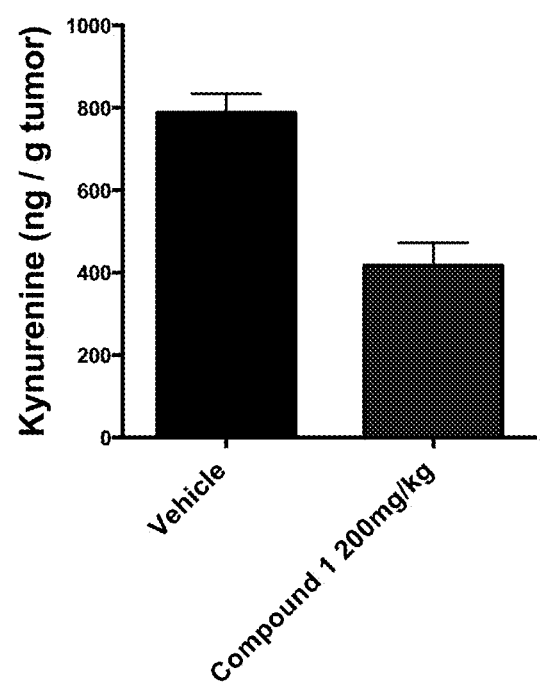
FIG. 5 is a graph showing the concentration of Kynurenine within a 4T1 tumor in mice after treatment with compound 1 of the invention or with a vehicle.

Example II.6: In Vivo Efficacy Studies on Inhibition of Tryptophan Degradation in 4T1 Tumor Tissue Compounds of this invention are capable of lowering kynurenine concentration within mouse tumors, for example 4T1 syngeneic tumors of Balb/c mice implanted orthotopically in the mammary gland. One hundred thousand 4T1 breast cancer cells were implanted orthotopically within the mammary gland of 7 weeks old Balb/c mice (day 0). Animals were randomized based on tumor size when tumor average reached 60 mm$^3$ (day 6) into different treatment cohorts (n=10/group). Animals were treated with Methocel vehicle from day 6 to 26 until tumors reached a size comprised between 1500 and 2000 mm$^3$. Compound 1 was suspended into Methocel vehicle and sonicated before oral administration to animals using gavage needles. Methocel vehicle or 200 mg/kg of Compound 1 was administered orally twice per day (approximately at 9 am and 5 pm) on day 26 and 27 days. The next morning, treatment was administered and mice were sacrificed 4 h after Compound 1 administration. The tumor was removed, weighted and frozen on dry ice. Tumors were analyzed by LC/MS-MS for Kynurenine concentration. Compound 1 reduced Kynurenine concentration by 47% (p<0.0001): see Table below and FIG. 5.

| Treatment | Kynurenine concentration (ng/g tumor) Average ± SEM |
|---|---|
| Vehicle Methocel | 787.5 ± 46.2 |
| Compound 1 200 mg/kg | 417.2 ± 55.7 |

Example II.7: In Vivo Efficacy Studies on Inhibition of Tryptophan Degradation in CT26 Tumor Tissue A. Compounds of this Invention are Capable of Lowering Kynurenine Concentration within Mouse Tumors In the present study, CT26 syngeneic tumors were implanted subcutaneously in Balb-c mice. More particularly, Five hundred thousand (500,000) CT26 colon carcinoma cancer cells [CT26.WT, available from the ATCC® CRL-2628™] were implanted subcutaneously in 7 weeks old Balb/c mice (day 0). Animals were randomized based on tumor size when tumor average reached 150 mm³ (day 11) into different treatment cohorts (n=10/group). Compound 1 was suspended into Methocel™ (methylcellulose) vehicle and sonicated before oral administration to animals using gavage needles. Methocel vehicle or Compound 1 was administered orally twice per day (approximately at 9 am and 5 pm) at 200 mg/kg for 2 days to the mice, once the tumor reached a size comprised between 1500 and 2000 mm³. The next morning, treatment was administered and mice were sacrificed 2 h after Compound 1 administration. The tumor was removed, weighted and frozen on dry ice. Tumors were analyzed by LC/MS-MS for Kynurenine concentration.

Figure 6:
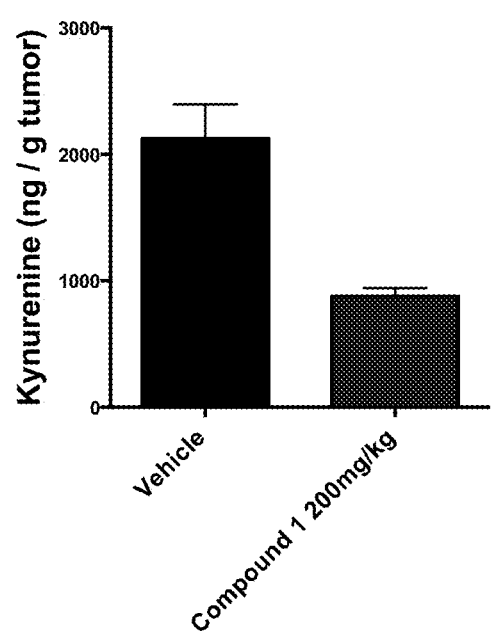
FIG. 6 is a graph showing the concentration of Kynurenine within a CT26 tumor in mice after treatment with compound 1 of the invention or with a vehicle.

Compound 1 reduced Kynurenine concentration by 59% (p<0.0001): see Table below and FIG. 6.

| Treatment | Kynurenine concentration (ng/g tumor) Average ± SEM |
|---|---|
| Vehicle Methocel | 2124 ± 272 |
| Compound 1 200 mg/kg | 876 ± 68 |

B. Compound 1 Inhibits Tumor Growth In Vivo

Figure 7:
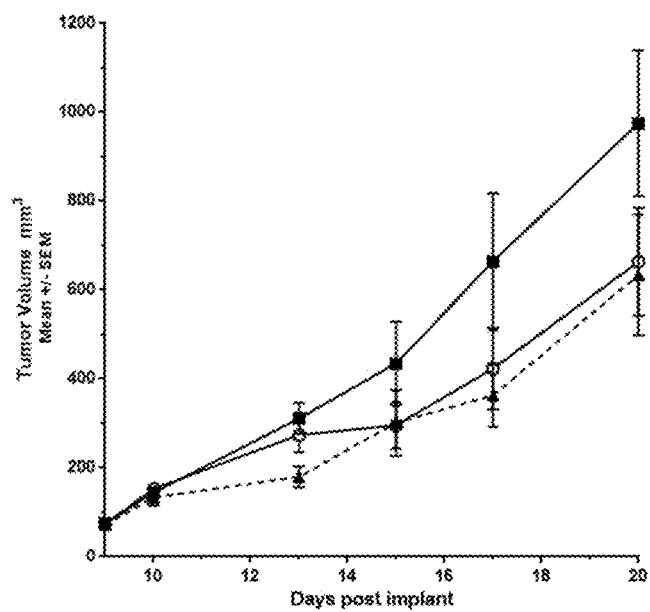
FIG. 7 is a graph showing the tumor growth of CT26 tumors in Balb/c mice in test Compound 1 at 200 mg/kg BID (open circle), 600 mg/kg BID (closed triangle), as compared to vehicle (square).

In a separate study, anti-tumor efficacy of IDO-1 inhibition was tested in the colon syngeneic mouse tumor model CT26 with a range of different treatment regimens. The model was essentially as described above, except that 1×10⁶ cells in phosphate buffered saline (PBS) were implanted subcutaneously in the flank of 8 week old Balb/c females on day 0 (10 in each group). Mice were randomized into treatment groups (100 mg/kg BID, 200 mg/kg BID or 600 mg/kg BID) based on tumor size on day 9 when treatment started. The results are shown the following table and in FIG. 7.

| Group | Dose mg/kg | Schedule | % TGI (D 15) | % TGI (D 17) | % TGI (D 20) | N |
|---|---|---|---|---|---|---|
| Vehicle | — | BID | — | — | — | 10 |
| Compound 1 | 100 | BID | 29 | 33 | 20 | 10 |
| Compound 1 | 200 | BID | 38 | 41 | 34 | 10 |
| Compound 1 | 600 | BID | 36 | 51 | 38 | 10 |

At the highest dose of 600 mg/kg, BID a significant tumor growth inhibition (TGI) of up to 51%. At lower doses of 100 and 200 mg/kg BID, TGIs based on the group averages of tumor measurements are slightly lower and thus suggest a dose proportionality.

All publications cited in this specification and priority applications including U.S. patent application Ser. No. 14/711,911, filed May 14, 2015 and U.S. Provisional Patent Application No. 61/996,976, filed May 15, 2014, are incorporated herein by reference. While the invention has been described with reference to particular embodiments, it will be appreciated that modifications can be made without departing from the spirit of the invention. Such modifications are intended to fall within the scope of the appended claims.

The invention claimed is:

1. A method for inhibiting IDO1 or treating a patient having cancer alleviated by inhibition of IDO1, said method comprising delivering a compound of Formula I to the patient in need thereof:

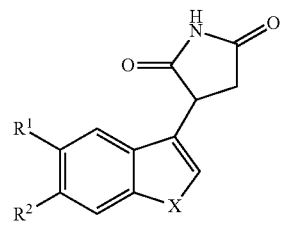

and pharmaceutically acceptable enantiomers, salts, solvates and prodrugs thereof, wherein:

X represents —NQ¹- or —CQ²=CQ³-;

Q¹, Q² and Q³ each independently represent H or alkyl

R¹ and R² each independently represent H, halo, cyano, alkyl or alkoxy.

2. The method according to claim 1, wherein Q¹, Q² and Q³ each independently represent H or methyl.

3. The method according to claim 1, wherein Q¹, Q² and Q³ each represent H.

4. The method according to claim 1, wherein Q¹ is H, X represents —NH—.

5. The method according to claim 4, wherein Q² and Q³ each independently represent H or alkyl.

6. The method according to claim 4, wherein Q² and Q³ each independently represent H or methyl.

7. The method according to claim 5, wherein Q² and Q³ each represent H.

8. The method according to claim 1, wherein R¹ and R² each independently represent H, halo, cyano, alkyl or alkoxy.

9. The method according to claim 8, wherein R¹ and R² each independently represent H or halo.

10. The method according to claim 9, wherein the halo is F.

11. The method according to claim 1, wherein the compound of Formula I is selected from: a compound of Formula I', a compound of Formula I", a racemic mixture of Formula I' and I", or a non-racemic mixture of Formula I' and formula I":

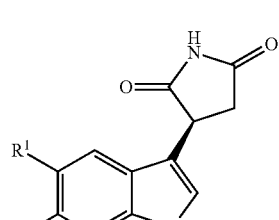

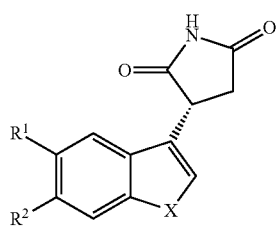

or a pharmaceutically acceptable enantiomer, salt, solvate or prodrug thereof, wherein:
X represents —NH—;
Q² and Q³ each independently represent H or C1 to C6 alkyl;
R¹ and R² each independently represent H, halo, cyano, C1 to C6 alkyl or C1 to C6 alkoxy;
and at least one pharmaceutically acceptable carrier.

12. The method according to claim 11, wherein the method comprises delivering approximately equal molar amounts of the compound of Formula I' and the compound of Formula I".

13. The method according to claim 11, wherein the method comprises delivering different molar amounts of the compound of Formula I' and the compound of Formula I".

14. The method according to claim 13 wherein the method comprises delivering a mixture of the compound of Formula I' and the compound of Formula I", wherein the composition comprises greater than 50% of a compound of Formula I'.

15. The method according to claim 14 wherein the method comprises delivering at least 95% to 100% of the compound of Formula I'.

16. The method according to claim 11, wherein the compound of Formula I' is selected from the group consisting of:
(a) (−)-(R)-3-(5-fluoro-1H-indol-3-yl)pyrrolidine-2,5-dione;
(b) (−)-(R)-3-(1H-indol-3-yl)pyrrolidine-2,5-dione;
(c) (−)-(R)-3-(5-chloro-1H-indol-3-yl)pyrrolidine-2,5-dione;
(d) (R)-3-(6-chloro-5-fluoro-1H-indol-3-yl)pyrrolidine-2,5-dione; and
(e) (R)-3-(6-bromo-5-fluoro-1H-indol-3-yl)pyrrolidine-2,5-dione,
or a pharmaceutically acceptable salt or solvate of any of (a) to (e).

17. The method according to claim 11, which comprises delivering a racemic mixture of a compound of Formula I' and Formula I", wherein the racemate is selected from the group consisting of:
3-(5-fluoro-1H-indol-3-yl)pyrrolidine-2,5-dione;
3-(1H-indol-3-yl)pyrrolidine-2,5-dione;
3-(5-chloro-1H-indol-3-yl)pyrrolidine-2,5-dione;
3-(6-chloro-5-fluoro-1H-indol-3-yl)pyrrolidine-2,5-dione;
3-(6-bromo-5-fluoro-1H-indol-3-yl)pyrrolidine-2,5-dione;
3-(5-bromo-1H-indol-3-yl)pyrrolidine-2,5-dione;
3-(5-methyl-1H-indol-3-yl)pyrrolidine-2,5-dione;
3-(5-methoxy-1H-indol-3-yl)pyrrolidine-2,5-dione;
3-(2,5-dioxopyrrolidin-3-yl)-1H-indole-5-carbonitrile;
3-(5,6-difluoro-1H-indol-3-yl)pyrrolidine-2,5-dione;
3-(5-fluoro-6-methyl-1H-indol-3-yl)pyrrolidine-2,5-dione;
3-(6-fluoro-1H-indol-3-yl)pyrrolidine-2,5-dione;
3-(6-chloro-1H-indol-3-yl)pyrrolidine-2,5-dione;
3-(6-bromo-1H-indol-3-yl)pyrrolidine-2,5-dione;
3-(6-methyl-1H-indol-3-yl)pyrrolidine-2,5-dione;
3-(6-methoxy-1H-indol-3-yl)pyrrolidine-2,5-dione;
3-(2,5-dioxopyrrolidin-3-yl)-1H-indole-6-carbonitrile;
3-(naphthalen-1-yl)pyrrolidine-2,5-dione;
3-(6-fluoronaphthalen-1-yl)pyrrolidine-2,5-dione;
3-(7-fluoronaphthalen-1-yl)pyrrolidine-2,5-dione;
3-(6-chloronaphthalen-1-yl)pyrrolidine-2,5-dione; or
3-(7-chloronaphthalen-1-yl)pyrrolidine-2,5-dione.

18. The method according to claim 11, wherein the compound of formula I" is selected from the group consisting of:
(a") (S)-3-(5-fluoro-1H-indol-3-yl)pyrrolidine-2,5-dione;
(b") (S)-3-(1H-indol-3-yl)pyrrolidine-2,5-dione;
(c") (S)-3-(5-chloro-1H-indol-3-yl)pyrrolidine-2,5-dione;
(d") (S)-3-(6-chloro-5-fluoro-1H-indol-3-yl)pyrrolidine-2,5-dione; and
(e") (S)-3-(6-bromo-5-fluoro-1H-indol-3-yl)pyrrolidine-2,5-dione, or a pharmaceutically acceptable salt or solvate thereof.

19. The method according to claim 1, wherein the compound delivered has structure of Formula II':

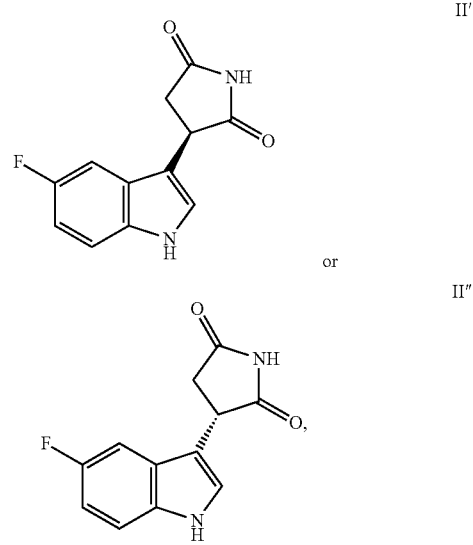

or a racemate thereof, or pharmaceutically acceptable salt thereof, or optionally comprising delivering a non-racemic mixture of the compounds.

20. The method according to claim 1, wherein the compound of Formula II' and the compound of Formula II" are present in a molar ratio of about 1:1.

21. The method according to claim 20, wherein at least about 75 mol % of the compound of Formula II' is delivered.

22. The method according to claim 21, wherein at least about 90 mol % of the compound of Formula II' is delivered.

23. A method for treating a patient having cancer associated with IDO1, said method comprising delivering a compound of Formula I to the patient in need thereof:

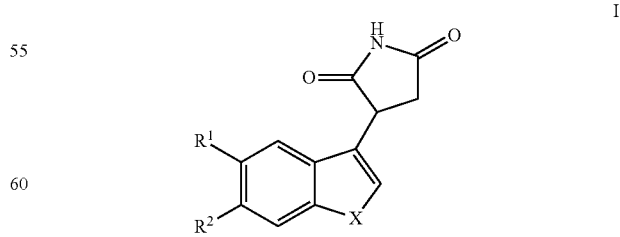

and pharmaceutically acceptable enantiomers, salts, solvates and prodrugs thereof, wherein:
X represents —NQ¹- or -CQ²=CQ³-;
Q¹, Q² and Q³ each independently represent H or alkyl $R^1$ and $R^2$ each independently represent H, halo, cyano, alkyl or alkoxy, preferably $R^1$ and $R^2$ each independently represent H or halo, wherein the cancer is selected from a malignant melanoma, acute myelogenous leukemia, pancreatic cancer, colorectal cancer, prostate cancer, cervical cancer, brain cancer, endometrial cancer and ovarian cancers.

24. The method according to claim 1, wherein R1 and R2 each independently represent H or halo.

* * * * *